(12) United States Patent
Geddes

(10) Patent No.: US 9,339,485 B2
(45) Date of Patent: *May 17, 2016

(54) PLASMONIC ENGINEERING OF SINGLET OXYGEN AND/OR SUPEROXIDE GENERATION

(75) Inventor: Chris D. Geddes, Bel-Air, MD (US)

(73) Assignee: UNIVERSITY OF MARYLAND, BALTIMORE COUNTY, Baltimore, MD (US)

( * ) Notice: Subject to any disclaimer, the term of this patent is extended or adjusted under 35 U.S.C. 154(b) by 1090 days.

This patent is subject to a terminal disclaimer.

(21) Appl. No.: 12/020,571

(22) Filed: Jan. 27, 2008

(65) Prior Publication Data
US 2008/0215122 A1 Sep. 4, 2008

Related U.S. Application Data

(60) Provisional application No. 60/904,501, filed on Mar. 2, 2007.

(51) Int. Cl.
| A61K 31/00 | (2006.01) |
| A61K 31/28 | (2006.01) |
| A61K 31/30 | (2006.01) |

(Continued)

(52) U.S. Cl.
CPC ............ *A61K 31/28* (2013.01); *A61K 31/30* (2013.01); *A61K 31/315* (2013.01); *A61N 5/0601* (2013.01); *A61N 5/062* (2013.01)

(58) Field of Classification Search
CPC ........................................... A61N 5/062
USPC ..................................... 607/88–94
See application file for complete search history.

(56) References Cited

U.S. PATENT DOCUMENTS

| 5,017,009 A | 5/1991 | Schutt et al. |
| 5,449,918 A | 9/1995 | Krull et al. |
| 5,866,433 A | 2/1999 | Schalkhammer et al. |

(Continued)

FOREIGN PATENT DOCUMENTS

| WO | 89/09408 | 10/1989 |
| WO | WO 2004/024191 | 3/2004 |

(Continued)

OTHER PUBLICATIONS

Sakamoto et al. "Synthesis of novel cationic amphiphilic phthalocyanine derivatives for next generation photosensitizer using photodynamic therapy of cancer" Dyes and Pigments 64 (2005) p. 63-71. Received Jan. 14, 2004; received in revised form Apr. 6, 2004; accepted Apr. 12, 2004, Available online Jul. 2, 2004.*

Lakowicz, Joseph R. "Radiative decay engineering 5: metal-enhanced fluorescence and plasmon emission." Anal. Biochem., 337(2): 171-194, Feb. 15, 2005.*

Demidova, T. N. & Hamblin, M. R. (2004) Photodynamic Therapy Targeted to Pathogens. *International Journal of Immunopathology and Pharmacology* 17, 245-254.

(Continued)

*Primary Examiner* — Lynsey Crandall
(74) *Attorney, Agent, or Firm* — Marianne Fuierer; Moore & Van Allen, PLLC

(57) ABSTRACT

The present invention provides for a method to increase the triplet yield of a photosensitizer by the coupling to metal surface plasmons which leads to increased singlet oxygen generation by electric field enhancement or enhanced energy absorption of the photosensitizer. The extent of singlet oxygen enhancement can be tuned for applications in singlet oxygen based clinical therapy by modifying plasmon coupling parameters, such as metallic nanoparticle size and shape, photosensitizer/metallic nanoparticle distance, and the excitation wavelength of the coupling photosensitizer.

16 Claims, 15 Drawing Sheets

(51) Int. Cl.
  A61K 31/315 (2006.01)
  A61N 5/06 (2006.01)

(56) References Cited

U.S. PATENT DOCUMENTS

| | | | |
|---|---|---|---|
| 6,428,811 B1* | 8/2002 | West et al. | 424/497 |
| 7,253,452 B2 | 8/2007 | Steckel et al. | |
| 7,348,182 B2 | 3/2008 | Martin et al. | |
| 7,351,590 B2 | 4/2008 | Martin | |
| 7,648,834 B2 | 1/2010 | Moore | |
| 7,718,445 B2 | 5/2010 | Martin | |
| 2003/0228682 A1 | 12/2003 | Lakowicz et al. | |
| 2004/0160606 A1 | 8/2004 | Lakowicz et al. | |
| 2005/0058713 A1* | 3/2005 | Russell et al. | 424/489 |
| 2006/0019279 A1* | 1/2006 | Bosse et al. | 435/6 |
| 2006/0147927 A1 | 7/2006 | Geddes et al. | |
| 2007/0037215 A1* | 2/2007 | Patton | 435/7.1 |
| 2007/0141163 A1* | 6/2007 | Vitaliano et al. | 424/490 |
| 2007/0269826 A1 | 11/2007 | Geddes | |
| 2008/0096281 A1 | 4/2008 | Geddes et al. | |
| 2009/0004461 A1 | 1/2009 | Geddes et al. | |
| 2009/0022766 A1 | 1/2009 | Geddes | |

FOREIGN PATENT DOCUMENTS

| | | |
|---|---|---|
| WO | WO 2006/074130 | 7/2006 |
| WO | WO 2006/137945 | 12/2006 |
| WO | WO 2006/138698 | 12/2006 |
| WO | WO 2007/053201 | 5/2007 |
| WO | WO 2007/095527 | 8/2007 |
| WO | WO 2008/048221 | 4/2008 |
| WO | WO 2008/151247 | 12/2008 |

OTHER PUBLICATIONS

Vrouenraets MB, Visser GWM, Snow GB, Van Dongen GAMS (2003) Basic principles, applications in oncology and improved selectivity of photodynamic therapy. Anticancer Res 23:505-522.
Wilson BC (2002) Photodynamic therapy for cancer: principles. Can J Gastroenterol 16(6):393-396.
Dolmans DE, Fukumura D, Jain RK (2003) Photodynamic therapy for cancer. Nat Rev Cancer 3(5):380-387.
Anantha, V. & Taflove, A. (2002) Efficient modeling of infinite scatterers using a generalized total-field/scattered field FDTD boundary. Ieee Transactions on Antennas and Propagation 50, 1337-1349.
Aslan, K., Wu, M., Lakowicz, J. R., & Geddes, C. D. (2007) Fluorescent core-shell Ag@SiO nanocomposites for metal-enhanced fluorescence and single nanoparticle sensing platforms. J Am Chem Soc 129, 1524-1525.
Aslan, K., Gryczynski, I., Malicka, J., Matveeva, E., Lakowicz, J. R., & Geddes, C. D. (2005) Metal-enhanced fluorescence: an emerging tool in biotechnology. Current Opinion in Biotechnology 16, 55-62.
Xu, H. X., Wang, X. H., Persson, M. P., Xu, H. Q., Kall, M., & Johansson, P. (2004) Unified treatment of fluorescence and raman scattering processes near metal surfaces. Physical Review Letters 93.
Aslan K, Previte M J R, Zhang YX, & CD, G. (2007) 2007 Biophysical Society Meeting Abstracts. Biophysical Journal, Supplement, Abstract, 317A.
Zhang, Y. X., Aslan, K., Previte, M. J. R., Malyn, S. N., & Geddes, C. D. (2006) Journal of Physical Chemistry B 110, 25108-25114.
Stiel, H., Teuchner, K., Paul, A., Leupold, D., & Kochevar, I. E. (1996) Quantitative comparison of excited state properties and intensity-dependent photosensitization by rose bengal. Journal of Photochemistry and Photobiology B: Biology 33, 245-254.
Flors, C., Fryer, M. J., Waring, J., Reeder, B., Bechtold, U., Mullineaux, P. M., Nonell, S., Wilson, M. T., & Baker, N. R. (2006) Imaging the production of singlet oxygen in vivo using a new fluoresencent sensor-singlet oxygen sensor green. Journal of Experimental Botany 57, 1725-1734.
Hideg, E., Barta, C., Kalai, T., Vass, I., Hideg, K., & Asada, K. (2002) Detection of singlet oxygen and superoxide with fluorescent sensors in leaves under stress by photoinhibition of UV radiation. Plant & cell physiology 43, 1154-1164.

Redmond, R. W. & Gamlin, J. N. (1999) A complication of singlet oxygen yields from viologically relevant molecules. Photochemistry and Photobiology 70, 391-475.
Hao, E. & Schatz, G. C. (2004) Electromagnetic fields around silver nanoparticles and dimmers. Journal of Chemical Physics 120, 357-366.
Foteinopoulou, S., Vigneron, J. P., & Vandenbem, C. (2007) Optical near-field exciations on plasmonic nanoparticle-based structures. Optics Express 15, 4253-4267.
Zhang, Y., Aslan, K., Malyn, S. N., & Geddes, C. D. (2006) Metal-enhanced phosphorescence. Chemical Physics Letters 427, 432-437.
Zhang, Y., Aslan, K., Previte, M. J. R., Malyn, S. N., & Geddes, C. D. (2006) Metal-enhanced phosphorescence: interpretation in terms of triplet-coupled radiating plasmons. Journal of Physical Chemistry B 110, 25108-25114.
Zhang, Y. X., Aslan, K., Previte, M. J. R., & Geddes, C. D. (2007) metal-enhanced singlet oxygen generation: a consequence of Plasmon enhanced triplet yields. Journal of Fluorescence 17, 345-349.
Barber, P. W., Chang, R. K., & Massoudi, H. (1983) Electrodynamic calculations of the surface-enhanced electric intensities on large Ag spheroids. Physical Review B 27, 7251-7261.
Yang, W. H., Schatz, G. C., & Vanduyne, R. P. (1995) Discrete dipole approximation for calculating extinction and Raman intensities for small particles with arbitrary shapes. Journal of Chemical Physics 103, 869-875.
Yee, K. S. & Chen, J. S. (1997) impedance boundary condition simulation in the FDTD/FVTD hybrid. Ieee Transactions on Antennas and Propagation 45, 921-925.
Moan, J., Peng, Q., Sorensen, R., Iani, V., & Nesland, J. M. (1998) The biophysical foundations of photodynamic therapy. Endoscopy 30, 387-391.
Jarvi, M. T., Niedre, M. J., Patterson, M. S., & Wilson, B. C. (2006) Singlet oxygen luminescence dosimetry (SOLD) for photodynamic therapy: current status, challenges, and future prospects. Photochemistry and Photobiology 82, 1198-1210.
Dougherty, T. J. (2002) An update on photodynamic therapy applications. Journal of Clinical Laser Medicine & Surgery 20, 3-7.
Kendall, C. A. & Morton, C. A. (2003) Photodynamic therapy for the treatment of skin disease. Technology in Cancer Research & Treatment 2, 283-288.
Brown, S. B., Brown, E. A., & Walker, I. (2004) The present and future role of photodynamic therapy in cancer treatment. Lancet Oncology 5, 497-508.
Kelly, K. L., Coronado, E., Zhao, L. L., & Schatz, G. C. (2003) The optical properties of metal nanoparticles: the influence of size, shape and dielectric environment. Journal of Physical Chemistry B 107, 668-677.
Challener, W. A., Sendur, I. K., & Peng, C. (2003) Scattered field formulation of finte difference time diomain for a focused light beam in dense media with lossy materials. Opt. Express 11, 3160-3170.
Yee, K. S. (1966), Numerical solution of initial boundary value problems involving maxwell's equations in isotropic media. IEEE Transactions on Antennas and Propagation 14, 302-307.
Aslan, K., Leonenko, Z., Lakowicz, J. R., & Geddes, C. D. (2005) Annealed silver-island films for applications in metal-enhanced fluorescence: interpretation in terms of radiating plasmons. Journal of Fluorescence 15, 643-654.
Geddes, C. D. & Lakowicz, J. R. (2002) Metal-enhanced fluorescence. Journal of Fluorescence 12, 121-129.
Thompson, M. S., Johansson, A., Johansson, T., Andersson-Engels, S., Svanberg, S., Bendsoe, N., & Svanberg, K. (2005) Clinical system for interstitial photodynamic therapy with combined on-line dosimetry measurements. Applied Optics 44, 4023-4031.
Bauer, J., Chen, K. H., Hiltbunner, A., Wehrli, E., Eugster, M., Schnell, D., & Kessler, F. (2000) The major protein import receptor of plastids is essential for chloroplast biogenesis. Nature 403, 203-207.

* cited by examiner

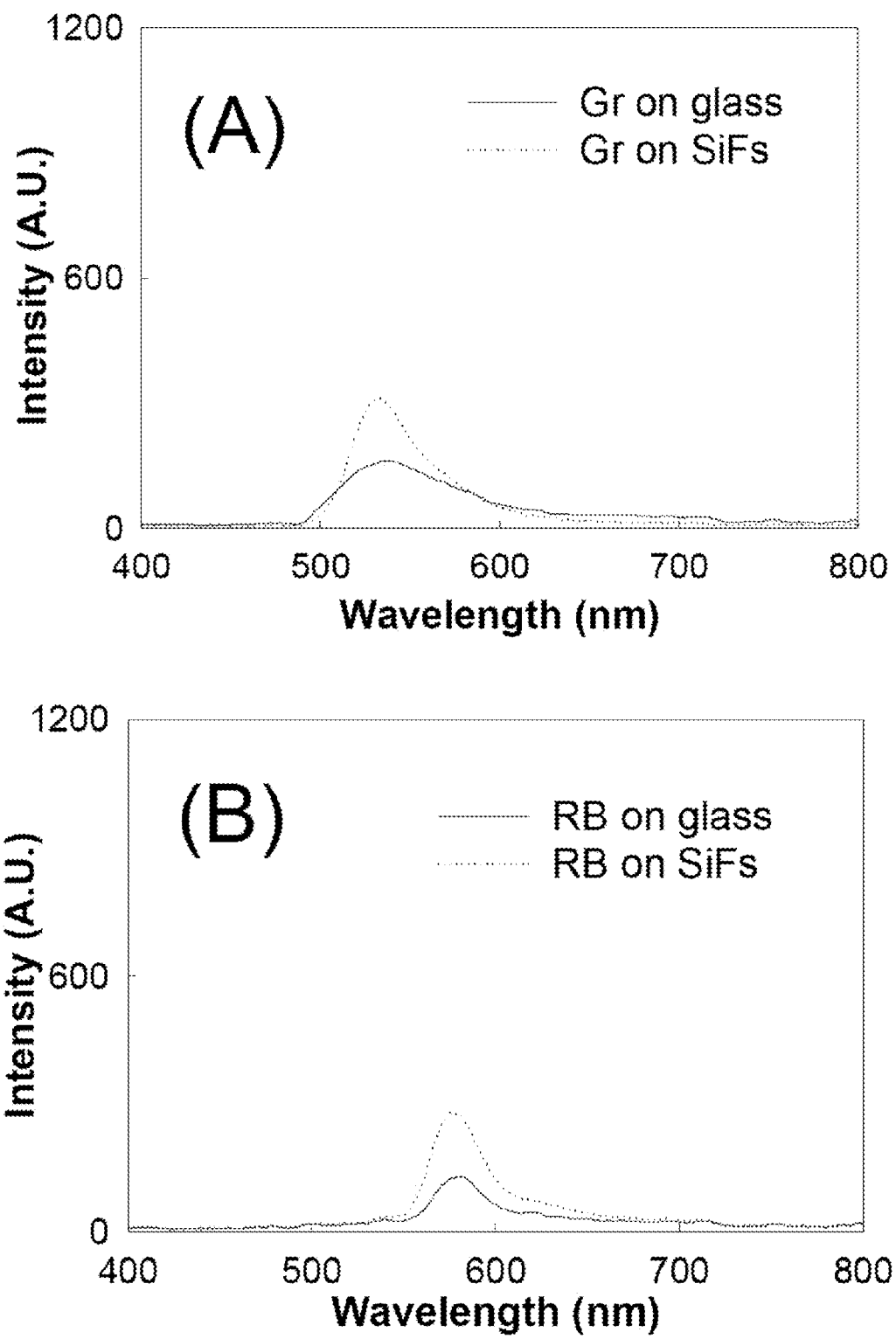
Figures 2 A and B

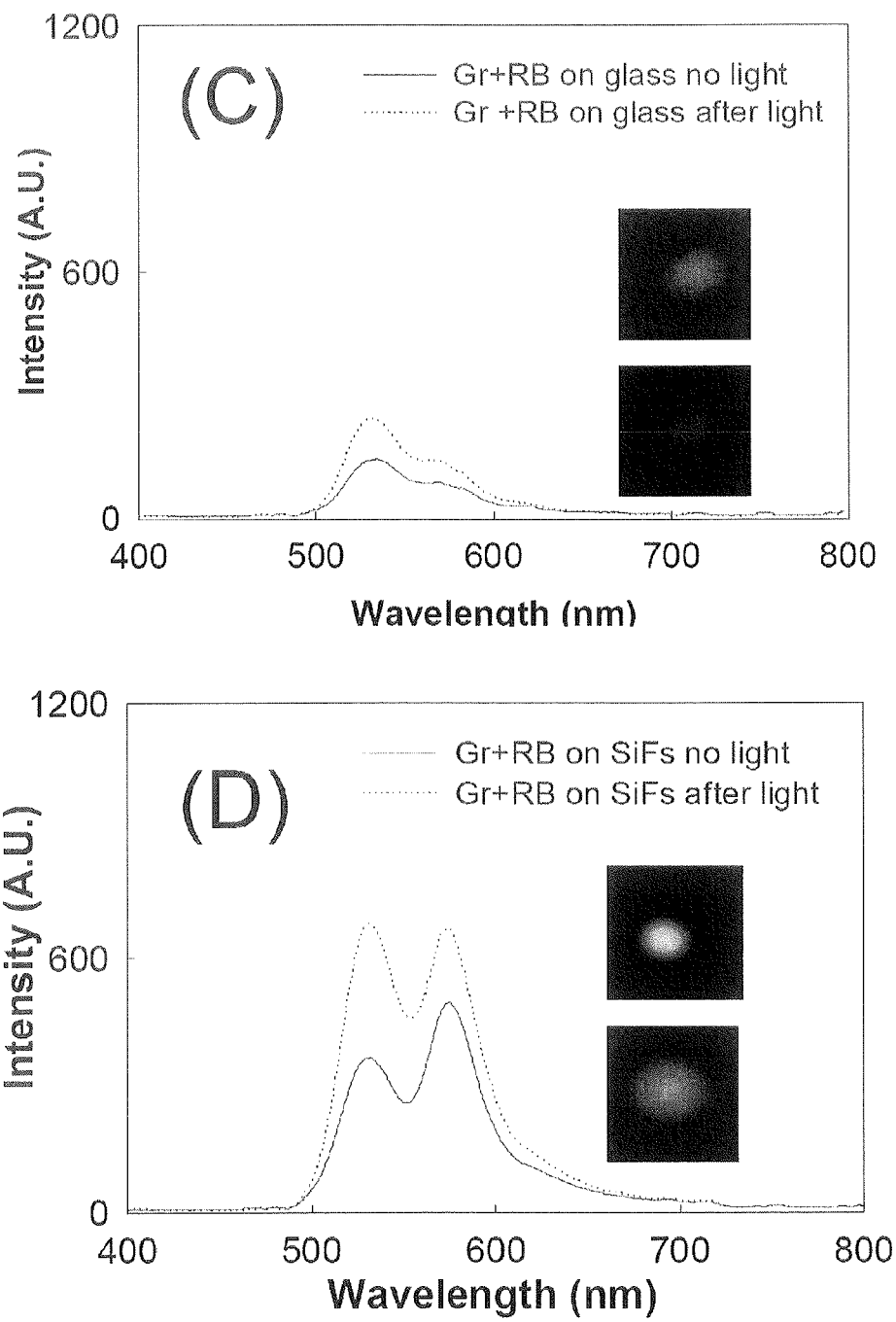
Figures 2C and D

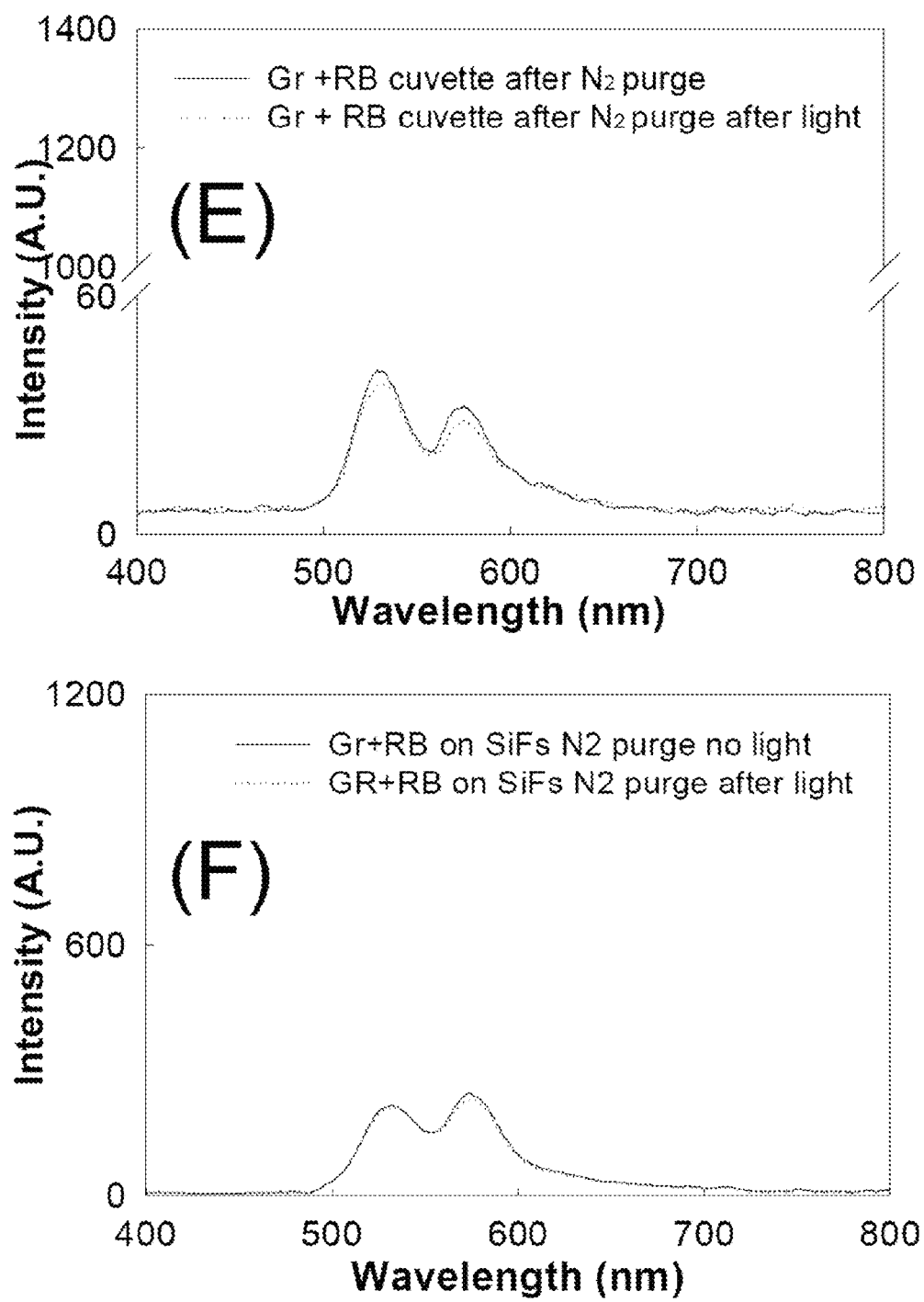
Figures 2 E and F

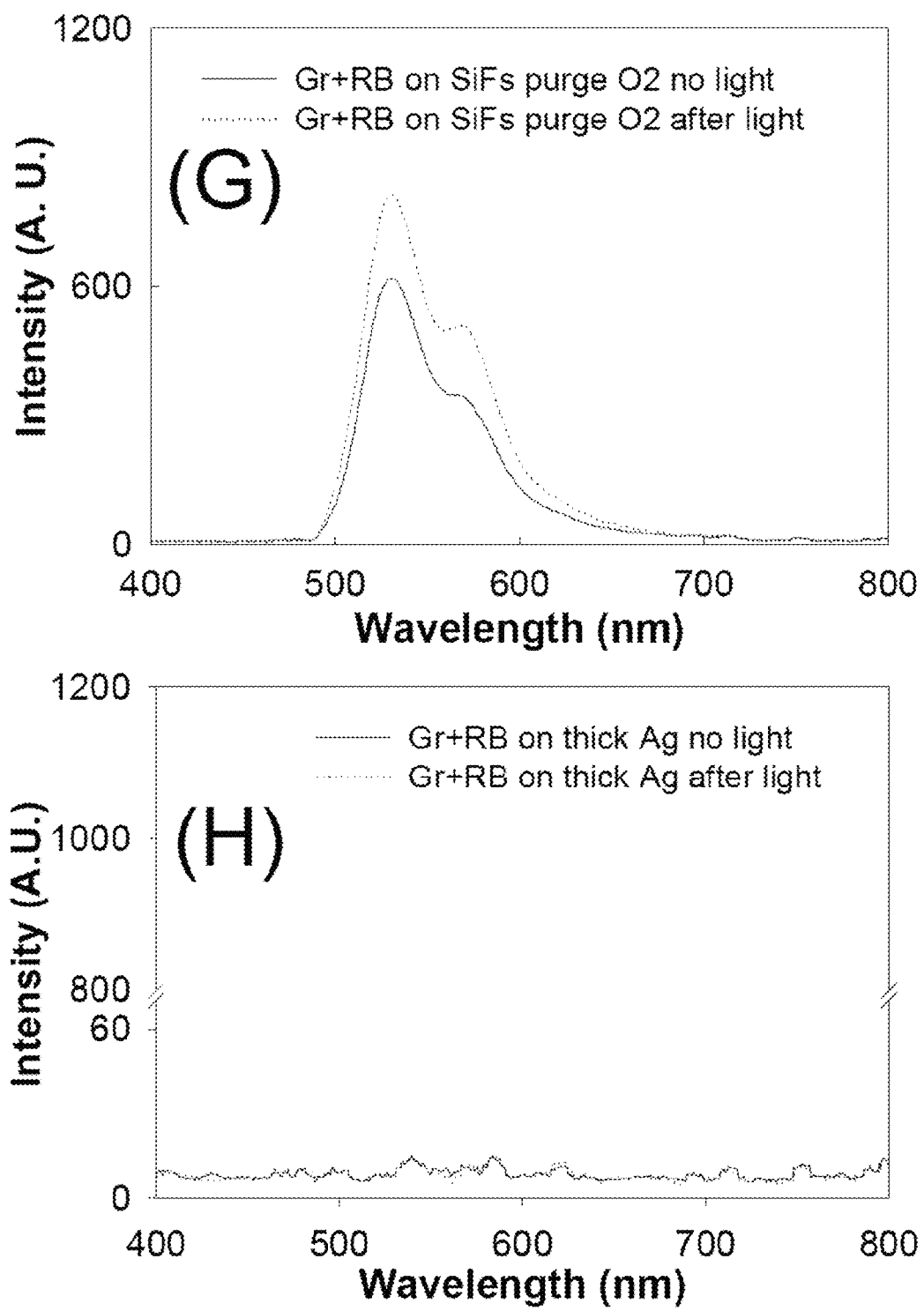
Figures 2G and H

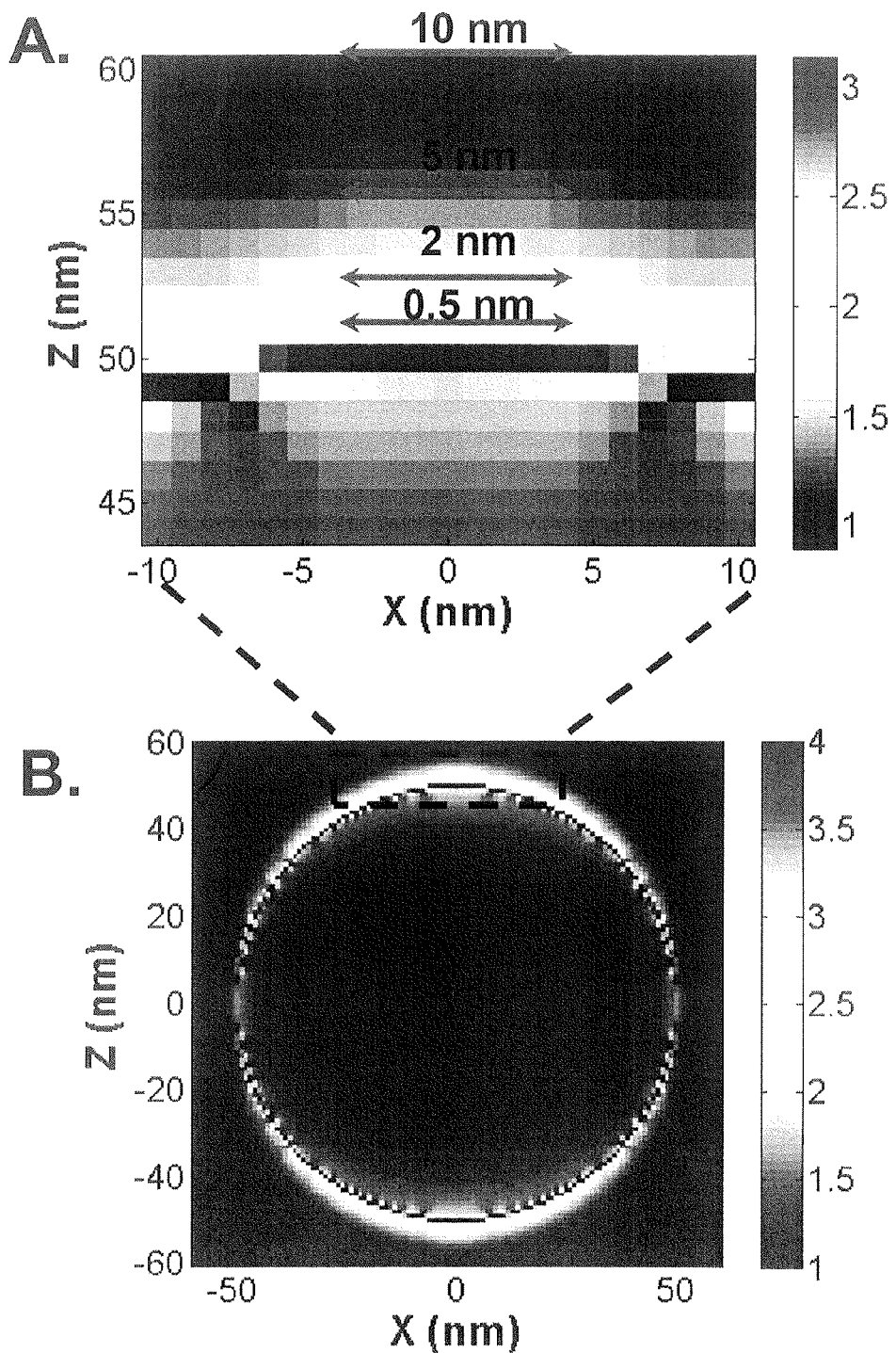
Figures 5A and B

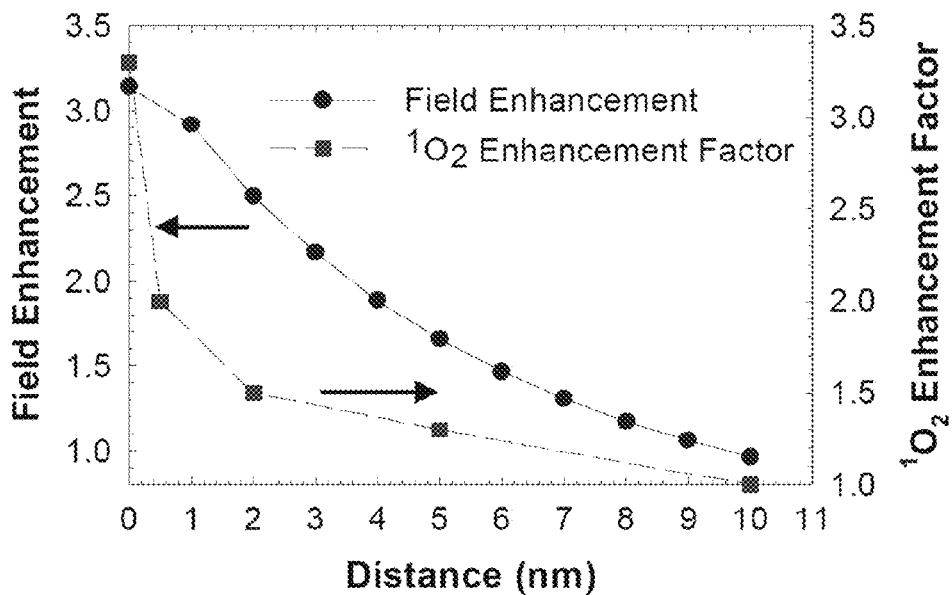
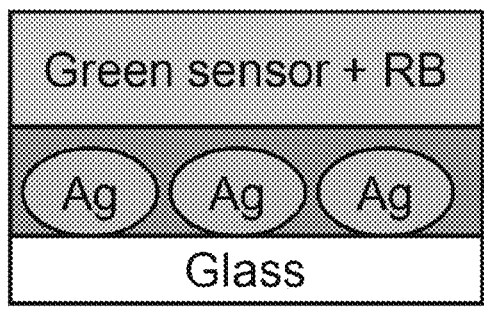
0 nm SiO$_x$ (EF = 3.3)
0.5 nm SiO$_x$ (EF = 2.0)
2 nm SiO$_x$ (EF = 1.5)
5 nm SiO$_x$ (EF = 1.3)
10 nm SiO$_x$ (EF = 1.0)
Figures 5 C and D

PLASMONIC ENGINEERING OF SINGLET OXYGEN AND/OR SUPEROXIDE GENERATION

CROSS-REFERENCE TO RELATED APPLICATIONS

This application claims priority to U.S. Provisional Application No. 60/904,501 filed in the United States Patent and Trademark Office on Mar. 3, 2007, the contents of which are hereby incorporated by reference herein for all purposes.

GOVERNMENT RIGHTS IN INVENTION

Work related to the invention was conducted in the performance of a grant from National Institute of Health RR008119. As a result of such contract, the U.S. Government has certain rights in the invention described herein.

BACKGROUND OF THE INVENTION

1. Field of the Invention

The invention relates to the generation of singlet oxygen, and more particularly, to methods and systems to increase the triplet yields of photosensitizers, by coupling to surface plasmons, which invariably results in more singlet oxygen generation.

2. Related Art

Molecular oxygen has a unique electronic configuration characterized by a partially filled set of antibonding $\pi^*$ orbitals. As predicted by Hund's rule, the lowest energy state of the molecular oxygen has maximum multiplicity, i.e. is a triplet ground state. Molecules whose outermost pair of electrons have parallel spins (symbolized by ↑↑) are in the "triplet" state; molecules whose outermost pair of electrons have anti-parallel spins (symbolized by ↑↓) are in the "singlet" state. Ground-state oxygen is in the triplet state indicated by the superscripted "3" in $^3O_2$, —its two unpaired electrons have parallel spins, a characteristic that, according to rules of physical chemistry, does not allow them to react with most molecules. Thus, ground-state or triplet oxygen is not very reactive. However, triplet oxygen can be activated by the addition of energy, and transformed into reactive oxygen species $^1O_2$ having a lifetime of approximately 45 minutes.

If triplet oxygen absorbs sufficient energy to reverse the spin of one of its unpaired electrons, it forms the singlet state. Singlet oxygen, abbreviated $^1O_2^*$, has a pair of electrons with opposite spins; though not a free radical it is still highly reactive. (The * symbol is used to indicate that this is an excited state with excess energy)

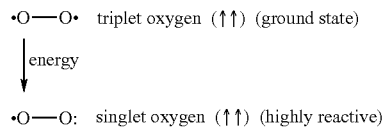

The physical, chemical and biological properties of singlet oxygen attracted serious attention from researchers during the 1960's despite its discovery in 1924. Since singlet oxygen can readily react with many biological targets and destroy a wide variety of cells, the photosensitized production of singlet oxygen has significance in a range of areas, especially in photodynamic therapy (PDT).

Photodynamic therapy (PDT) has been widely used in both oncological, (e.g. tumors and dysplasias) and nononcological (e.g. age-related macular degeneration, localized infection and non-malignant skin conditions) applications.(1-4) PDT is applied in multiple steps for the treatment of patients with cancer. Three primary components are involved in PDT: light, a photosensitizing drug and oxygen. In the first step, a photosensitizing agent is deposited on/or near surface tumors after its injection into the bloodstream. Then, the photosensitizer-deposited cancer tumor is exposed to light. Here, the excited photosensitizer transfers its energy to molecular oxygen while returning to the ground state, which results in the production of singlet oxygen. Subsequently, singlet oxygen destroys nearby cancer cells.(1) The singlet oxygen is a cytotoxic agent and reacts rapidly with cellular components to cause damage that ultimately leads to cell death and tumor destruction.(4) PDT treatments are only effective within a specific range of singlet oxygen supply.(5)

Triplet oxygen can also be activated by the addition of energy, in the form of a single electron to form a triplet oxygen called superoxide, abbreviated $O_2^{.-}$.

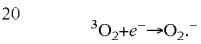

Superoxide is a radical that is a precursor to other oxidizing agents, including singlet oxygen. Superoxide can react with the hydroxyl radical (HO.) to form singlet oxygen ($^1O_2^*$), as shown below:

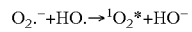

Currently, the intensity of light is commonly adjusted to control the extent of singlet oxygen generation, but there are some limitations to this method. High fluency rates of the exposure light will lead to oxygen depletion and photosensitizer photo-bleaching.(3) However, low fluency rates of exposure light, lends to a long exposure time and can cause vascular shutdown, a precursory condition to hypoxia in the tissue.(5,7) One notable approach to control the fluency rate of exposure light is called interstitial PDT, where precise amount of light is delivered locally to tumors through inserted optical fibers.(8) The interstitial PDT also allows the real-time monitoring of the progression of the treatment via online collection of assessment parameters through the optical fibers.(8) It is important to note that despite the better control over fluency rate the photobleaching of the photosensitizers remains an issue.

Since singlet oxygen plays a very important role in cell damage, an abundant supply of oxygen is required. However, photodynamic therapy is currently limited by the insufficient generation of singlet oxygen while reacting with biological targets and photobleaching of the photosensitizers remains an issue. Thus, it would be advantageous to provide a method to resolve these problems by increasing singlet oxygen generation and reduce photobleaching of the photosensitizer.

SUMMARY OF THE INVENTION

The present invention provides for a method to increase the triplet yield of photosensitizers by the coupling of absorbed energy by the photosensitizer to metal surface plasmons which leads to increased singlet oxygen generation.

In one aspect, the present invention provides for a method for increasing singlet oxygen generation in molecular oxygen, the method comprising:
(a) providing a surface substrate, wherein at least a section of the substrate is coated with a metallic material that exhibits surface plasmons on excitation;
(b) coupling a photosensitizer compound to the metallic material, wherein the photosensitizer is linked to a spacer to the metallic surface, attached to a surface coating covering the metallic material or impregnated into the surface coating and wherein the photosensitizer is positioned at a distance from the metallic material that provides for coupling interaction between the photosensitizer compound and excited metallic surface plasmons; and (c) irradiating the photosensitizer in an amount sufficient to increase triplet yield of the photosensitizer by coupling with the surface plasmons thereby providing for increased single oxygen generation in available molecular oxygen.

In another aspect, the present invention relates to a method for increasing singlet oxygen generation in molecular oxygen, the method comprising:

(a) providing a metallic core with a surface coating, wherein the metallic core exhibits surface plasmons on excitation;

(b) coupling a photosensitizer compound to the metallic material, wherein the photosensitizer is attached to a surface coating covering the metallic core or impregnated into the surface coating and wherein the photosensitizer compound is positioned at a distance from the metallic core to provide for coupling interaction between the photosensitizer compound and excited metallic surface plasmons; and (c) irradiating the photosensitizer compound in an amount sufficient to increase triplet yield of the photosensitizer compound by coupling with the surface plasmons thereby providing for increased single oxygen generation in a available molecular oxygen.

In a still further aspect, the present invention provides for a photodynamic treatment to a site in need of such treatment in a subject to cause a desired therapeutic change, comprising the steps of:

(a) applying a photosensitizer complex to the treatment site in the presence of molecular oxygen, wherein the photosensitizer complex comprises:
  (i) a metallic core with a surface coating, wherein the metallic core exhibits surface plasmons on excitation; and
  (ii) a photosensitizer compound coupled to the metallic material, wherein the photosensitizer compound is attached to a surface coating covering the metallic core or impregnated into the surface coating and wherein the photosensitizer compound is positioned at a distance from the metallic core to provide for coupling interaction between the photosensitizer compound and excited metallic surface plasmons; and (b) positioning a light source that directly generates light having one or more emission wavelengths substantially equal to a wavelength of absorption of the photosensitive compound; and (c) administering the light to the site in an amount sufficient to increase triplet yield of the photosensitizer compound by coupling with the metallic surface plasmons thereby providing for increased singlet oxygen generation in the available molecular oxygen.

In a still further aspect, the present invention provides for a photosensitizer complex that enhances generation of singlet oxygen in molecular oxygen comprising:

(a) a metallic core with a surface coating, wherein the metallic core exhibits surface plasmons on excitation; and (b) a photosensitizer compound coupled to the metallic material, wherein the photosensitizer compound is attached to a surface coating covering the metallic core or impregnated into the surface coating and wherein the photosensitizer compound is positioned at a distance from the metallic core to provide for coupling interaction between the photosensitizer compound and excited metallic surface plasmons, thereby generating singlet oxygen in adjacent molecular oxygen.

The complex may further include binding ligands attached to surface coating or impregnated therein wherein the ligands have affinity for a receptor on a cell in need of photodynamic therapy. The photodynamic therapy can be applied in vivo or in vitro dependable on the available light source. Further the complex is sized for cellular entry and vascular diffusion.

The coating can be evenly distributed on the metallic core, in a pattern, or discontinuously distributed and having a thickness from about 0.5 nm to about 40 nm. The metallic core can be a solid metallic sphere or a core of one material that is coated with a metallic surface. Preferably the metallic sphere has a diameter ranging from about from about 2 nm to 150 nm and more preferably from about 20 to 100 nm. The metallic core may be fabricated from any metal that provides for excitable plasmons, and preferably, the metallic element is a metal such as silver, gold, platinum, aluminum, copper, zinc, palladium and composites thereof. The photosensitizer may be evenly distributed, randomly or patterned within or on the coating encompassing the metallic core.

In a still further aspect the present invention provides for a for a photosensitizer complex that enhances generation of singlet oxygen in molecular oxygen comprising:

(a) a surface substrate, wherein at least a section of the substrate is coated with a metallic material that exhibits surface plasmons on excitation; and (b) a photosensitizer compound coupled to the metallic material, wherein the photosensitizer compound is positioned at a distance from the metallic core to provide for coupling interaction between the photosensitizer compound and excited metallic surface plasmons, thereby generating singlet oxygen in adjacent molecular oxygen.

In another aspect, the photosensitizer complex of the present invention may also be conjugated with at least one targeting moiety, attached to the surface coating, surface substrate or metallic material depending on the fabrication of the complex, wherein the targeting moiety is specific for a cancer- and/or pathogen-specific marker on a tumor. The targeting moiety may include but is not limited to an antibody or fragment thereof, a protein or a fragment thereof, an antisense nucleic acid, a polypeptide, a peptide nucleic acid, or an oligonucleotide. Thus, upon administration to a subject, the photosensitizer complex will specifically bind to those cells and/or organisms that express the biological entity specific for the targeting moiety. The subject is then exposed to electromagnetic radiation at a frequency for absorption by the attached photosensitizer compound to be used for generating singlet oxygen and/or for tracking of the movement of the photosensitizer complex if a tracking fluorophore is also included on or in the surface coating. The target moiety may be attached to the surface coating through a linker, wherein the linker attaches the targeting moiety to the coating may include a lipid, a carbohydrate, a polysaccharide, a protein, a polymer, a glycoprotein, or a glycolipid.

Yet another aspect of the present invention provides for a method of producing light-induced singlet oxygen, the method comprising subjecting a photosensitizer complex to light in the presence of oxygen, wherein the photosensitizer complex comprises:

(a) a metallic core with a surface coating, wherein the metallic core exhibits surface plasmons on excitation; and (b) a photosensitizer compound coupled to the metallic material, wherein the photosensitizer compound is attached to a surface coating covering the metallic core or impregnated into the surface coating and wherein the photosensitizer compound is positioned at a distance from the metallic core to provide for coupling interaction between the photosensitizer compound and excited metallic surface plasmons, thereby generating singlet oxygen in adjacent molecular oxygen.

Another aspect of the present invention provides for a method of treating a host harboring neoplastic tissue, such as tumor cells, the method comprising administering to the host at least a first agent in the presence of light and molecular oxygen, wherein the first agent comprises a photosensitizer complex comprising;

(a) a metallic core with a surface coating, wherein the metallic core exhibits surface plasmons on excitation; and (b) a photosensitizer compound coupled to the metallic material, wherein the photosensitizer compound is attached to a surface coating covering the metallic core or impregnated into the surface coating and wherein the photosensitizer compound is positioned at a distance from the metallic core to provide for coupling interaction between the photosensitizer compound and excited metallic surface plasmons, thereby generating singlet oxygen in adjacent molecular oxygen that is cytotoxic to the neoplastic tissue.

A second agent may be administered simultaneously, previous to or subsequent to the administration of the first agent, wherein the second agent may be radiation therapy or a chemotherapy agent.

Other features and advantages of the invention will be apparent from the following detailed description, drawings and claims

BRIEF DESCRIPTION OF THE FIGURES

FIG. 2 shows fluorescence emission spectra of green sensor (Gr) (A) Rose Bengal (RB) (B) and a mixture of both on (C) glass, (D) SiFs, (E) in cuvette, (F) on SiFs nitrogen purged, (G) on SiFs oxygen purged, (H) on 50 nm thick Ag, before and after light exposure (2 min) at room temperature. Light source is 100 W mercury lamp. $\lambda_{ex}$=473 nm.

FIG. 5 shows FDTD calculations for field enhancements around silver sphere. (A) Zoomed image of 10 nm above the surface of the silver sphere maximum field intensity at z=10 nm to correlate increased field enhancements in proximity to sphere surface with increased singlet oxygen generation. (B) |E|2 field intensity (incident plus scatter) distribution in the xz plane around a 100 nm silver sphere due to an incident TFSF wave propagating along the y axis and polarized along the z axis with a wavelength of 365 nm, which corresponds to the max wavelength of the UV source used to excite Rose Bengal and generate singlet oxygen. (C) Distance dependence Relationship between for electric field enhancements and singlet Oxygen on 100 nm Ag nanoparticles. (D) Distance dependence of Singlet Oxygen Enhancement Factor of Rose Bengal on SiFs. Top layer is mixed solution of Green Sensor and Rose Bengal. $SiO_x$ layer was deposited using thermal vapor deposition. RB—Rose Bengal. Ag—Silver island Films. EF—Enhancement Factor.

DETAIL DESCRIPTION OF THE INVENTION

It is widely accepted that singlet oxygen is the primary cytotoxic agent responsible for photobiological activity. Since singlet oxygen plays a very important role in cell damage, an abundant supply of singlet oxygen is required. In addition, photodynamic therapy is currently limited by the insufficient generation of singlet oxygen while reacting with biological targets. A method to resolve these problems is to increase the triplet yield of sensitizers, by coupling to metallic surface plasmons, which invariably results in more singlet oxygen generation.

Thus, the present invention uses a metal-enhanced phenomenon as a means to control the extent of singlet oxygen generation via metal-photosensitizer interactions.

Figure 1:
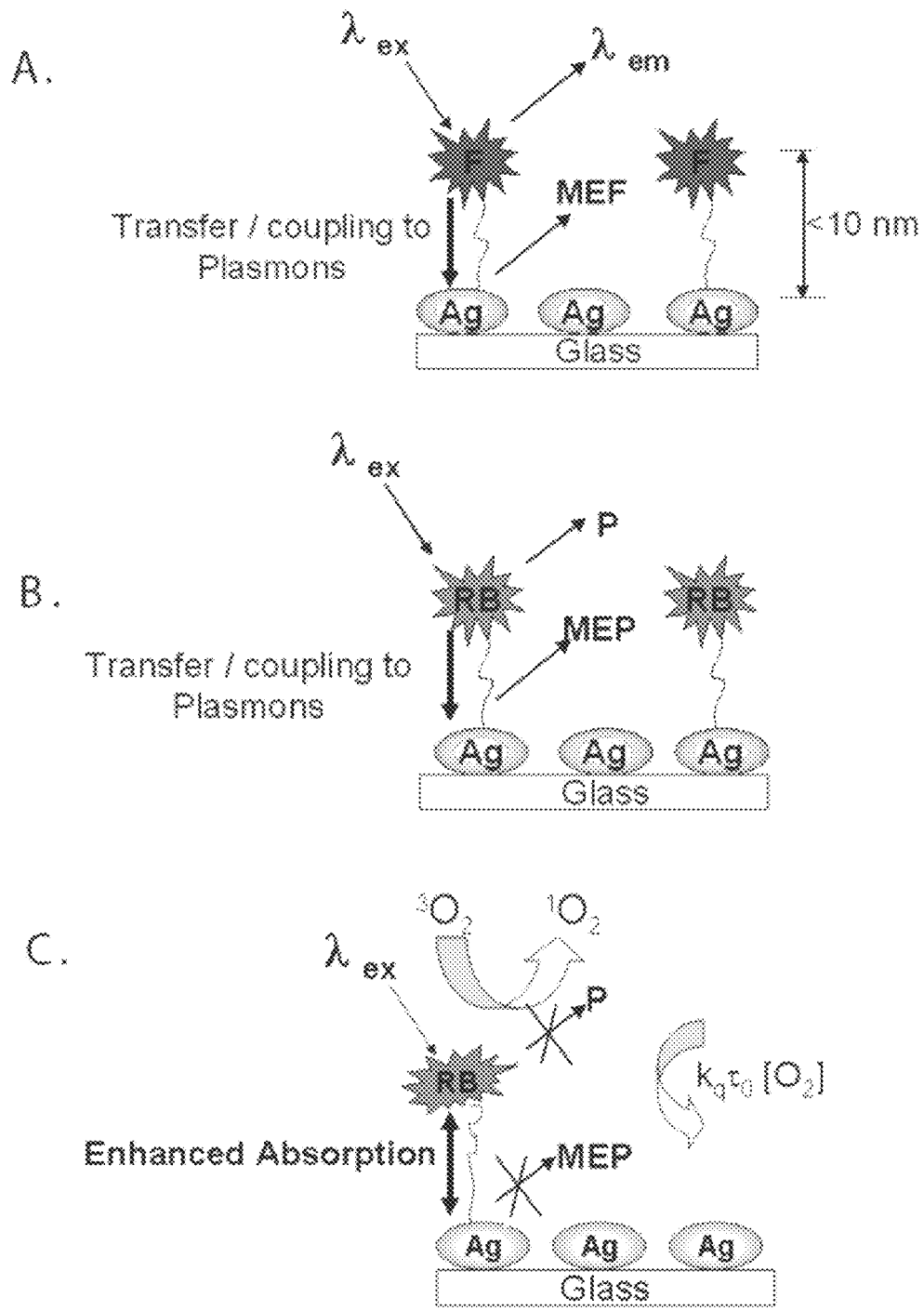
FIG. 1 shows a graphical representation of Metal-Enhanced Fluorescence (A), Metal-Enhanced Phosphorescence (B), and for the generation of Singlet Oxygen (C). F—Fluorophore, RB—Rose Bengal, P—Phosphorescence and MEP—Metal-Enhanced Phosphorescence, $^3O_2$—triplet ground state oxygen. $^1O_2$—singlet oxygen.

The present invention relates to the understanding that the near-field interactions of fluorophores with metallic nanoparticles causes a phenomena called metal-enhanced fluorescence (MEF).(9) According to present interpretation of MEF, as shown in FIG. 1 Top, non-radiative energy transfer occurs from excited distal fluorophores to the surface plasmon electrons on non-continuous films.(10) The surface plasmons in turn, radiate the photophysical characteristics of the coupling fluorophores.

Figure 6:
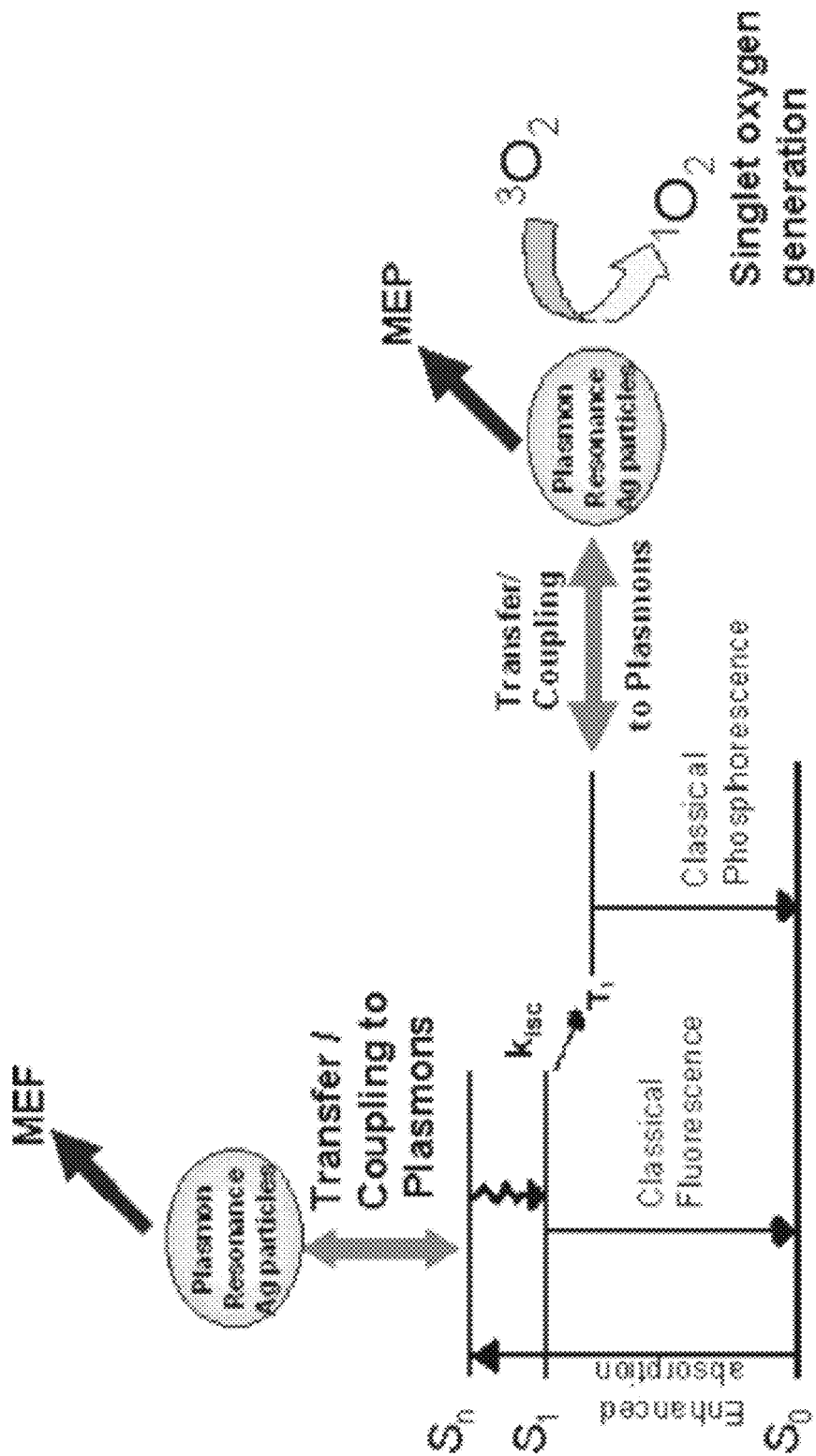
FIG. 6 is a schematic Jablonski diagram for the Photosensitizer and surface plasmon enhanced Singlet Oxygen generation. MEF—Metal Enhanced Fluorescence. MEP—Metal Enhanced Phosphorescence. $^3O_2$ triplet ground state oxygen. $^1O_2$ singlet oxygen. isc—intersystem crossing.

In addition to MEF, metal-enhanced phosphorescence (MEP) at low temperature has been observed(11,12), whereby non-radiative energy transfer is thought to occur from excited distal triplet-state luminophores to surface plasmons in non-continuous silver films, which in turn, radiate fluorophore/lumophore phosphorescence emission efficiently, as shown in FIG. 1—Middle. FIG. 1—Bottom shows a system wherein silver island films (SIF) enhance singlet oxygen generation as a result of the increase in the net system absorbance or enhanced triplet yield. FIG. 6 shows a modified Jablonski diagram showing the possible mechanisms for the fate of an excited fluorophore/lumophore when in close proximity to a plasmon resonance particle. Firstly, a photosensitizer is excited from the ground state $S_0$ to an excited state, $S_n$, where the metal readily allows for enhanced absorption i.e. an enhanced excitation rate. $S_n$ then relaxes to the lowest excited singlet state $S_1$, facilitating intersystem crossing. More singlet oxygen is subsequently generated due to the enhanced intersystem crossing and enhanced triplet yield.

It is theorized by the present inventor that the mechanism of singlet oxygen generation from the photo-sensitizer, which in FIG. 6 is Rose Bengal, is an energy transfer process during a collision of the excited lumophore with $^3O_2$. Since the lifetime of the triplet excited $T_1$ state (micro or milli-second range) is much longer than that of the singlet excited $S_1$ state (nanosecond), it is long enough for the triplet excited state to react with (ground-state triplet oxygen) $^3O_2$ to form $^1O_2$, in essence competing with the more favorable phosphorescence emission. Surprisingly, it has been found that the both MEP and ME$^1O_2$ are enhanced in the same system even though both processes are competitive and provide a route for the deactivation of electronic excited triplet states. As such, results set forth hereinbelow show that an enhanced absorption of a photosensitizer near to silver (11,12)(i.e. an enhanced excitation rate) can facilitate both MEP and ME$^1O_2$ simultaneously in the same system.

This observation of Metal-Enhanced $^1O_2$ generation is not only helpful to further the understanding of plasmon-lumophore interactions, but suggests that this approach may be of significance for singlet oxygen based clinical therapy wherein an abundant supply of $^1O_2$ is required (33-35).

Surface plasmons are collective oscillations of free electrons at metallic surfaces. When a metallic article or surface is exposed to an electromagnetic wave, the electrons in the metal (plasmons) oscillate at the same frequency as the incident wave. Subsequently, the oscillating electrons radiate electromagnetic radiation with the same frequency as the oscillating electrons. It is this re-radiation of light at the same incident wavelength that is often referred to as plasmon emission. In the present invention electromagnetically induced electronic excited states caused by exciting a photosensitizer couple to surface plasmons to produce emission intensities greater than from about 5 to 1000-fold, as compared to a control sample containing no metallic surface.

In one embodiment, the present invention relates to a metallic particle, such as a metallic sphere or core encompassed with a polymer or silica coating for positioning of at least a photosensitizer, fluorophore, luminophores or chemiluminescent species and wherein the photosensitizer, fluorophore, luminophores or chemiluminescent species are directly attached to the coating or impregnated within the coating. The coating can be evenly distributed on the metallic core, continuously, in a pattern, or discontinuously distributed and having a thickness from about 2 nm to about 40 nm. The metallic core can be any shape including sphere, rod, elliptical and can be a solid metallic core or a core of another material that is coated with a metallic surface. Preferably the metallic core has a diameter ranging from about from about 2 nm to 150 nm and more preferably from about 20 to 100 nm.

The thickness of the coating is generally the thickness to provide a distance wherein the photosensitizer is from about 5 nm to about 100 nm from the metal surfaces to provide optimal enhancement of triplet yield. Preferable distances are about 5 nm to about 50 nm depending on placement of the photosensitizer molecules including the use of a linker or whether it is impregnated into the coating. Thus, the thickness of the coating can be from about 5 nm to about 100 nm.

As stated above, the metallic core of the nanospheres of the present invention may be coated with a synthetic or naturally occurring polymer. Exemplary polymers useful in the present disclosure include, but are not limited to, polyesters, polyamides, polyethers, polythioethers, polyureas, polycarbonates, polycarbamides, proteins, polysaccharides, polyaryls, etc. The polymers useful in the coatings may include average molecular weights ranging from 100 g/mol to 100,000 g/mol, preferably 500 g/mol to 80,000 g/mol. Notably, the polymer may be a biodegradable polymer such as synthesized from monomers selected from the group consisting of D, L-lactide, D-lactide, L-lactide, D, L-lactic acid, D-lactic acid, L-lactic acid, glycolide, glycolic acid, hydroxybutyric acids, and malic acid.

In another embodiment the surface coating may be formed from an oxide containing compound or include an oxide containing compound. The oxide layer may be formed from a deposition technique, such as vapor deposition. The oxide layer coating may include at least one metal selected from the group consisting of Ti, Fe, Cu, Zn, Y, Zr, Nb, Mo, In, Si, Sn, Sb, Ta, W, Pb, Bi and Ce and having a valence of from 2 to 6. The form of the oxide of such a metal may, for example, be $SiO_2$, $TiO_2$, $Fe_2O_3$, CuO, ZnO, $Y_2O_3$, $ZrO_2$, $Nb_2O_5$, $MoO_3$, $In_2O_3$, $SnO_2$, $Sb_2O_5$, $Ta_2O_5$, $WO_3$, PbO or $Bi_2O_3$. These metal oxides may be used alone or in combination with other types of coatings. Preferably, the oxide is a silicon oxide, more preferably, $SiO_2$. The vapor deposition of $SiO_2$ is a well established technique for the controlled deposition of a variety of substrates. For example, an Edwards Vapor deposition module allows the deposition of an inert coating of $SiO_2$.

Method for fabrication of the metallic sphere is fully disclosed in copending application U.S. patent Ser. No. 12/016, 247 entitled "METAL-ENHANCED FLUORESCENCE NANOPARTICLES," the content incorporated by reference herein for all purposes.

The term "receptor-ligand" as used herein means any naturally occurring or unnaturally occurring binding couple wherein the components have affinity for each other. For example, the binding couple may include an antibody/antigen complex, viral coat ligand/protein cell receptor or any combination of probe and binding partner. The term "receptor" refers to a chemical group, molecule, biological agent, naturally occurring or synthetic that has an affinity for a specific chemical group, molecule, virus, probe or any biological agent target in a sample. The choice of a receptor-ligand for use in the present invention will be determined by nature of the disease, condition, or infection to be assayed.

"Fluorophore," as used herein, means any substance that emits electromagnetic energy such as light at a certain wavelength (emission wavelength) when the substance is illuminated by radiation of a different wavelength (excitation wavelength) and is intended to encompass a chemical or biochemical molecule or fragments thereof that is capable of interacting or reacting specifically with an analyte of interest in a sample to provide one or more optical signals. Additionally fluorophore includes both extrinsic and intrinsic fluorophores. Extrinsic fluorophore refer to fluorophores bound to another substance. Intrinsic fluorophores refer to substances that are fluorophores themselves. Exemplary fluorophores include but are not limited to those listed in the Molecular Probes Catalogue which is incorporated by reference herein.

"Photosensitizer" as used herein means any molecule that absorbs energy in the UV range, IR range of visible spectrum range, has a high triplet quantum yield and produces singlet oxygen. Examples of acceptable photosensitizers include but are not limited to Rose Bengal acetate, phthalocyanin (PC), hypericin, chlorin and bacteriochlorin derivatives, tetrapyrroles, Porphyrins and derivatives, Methyl 5-Aminolevulinate, Foscan, Levulan Kerastick, Metvix, Photofrin/Photobarr, Visudyne, Anthracyclines, Benzoporphyrin and Benzoporphyrin Derivatives, Phorbides, Porphycenes, Psoralens, Purpurins, Synthetic Nonporphyrin Compounds, Antrin, Litx, Mono-L-Aspartyl e6, Chlorin, Theralux, Indocyanine green or Visudyne.

The photosensitizing complexes of the present invention are thus useful in general, in the manner known in the art for sensitizing neoplastic cells or other abnormal tissue including infectious agents to destruction by irradiation using, preferably, visible light. Upon photoactivation, the energy of photoactivation is believed to be transferred to endogenous oxygen to convert it to singlet oxygen. This singlet oxygen is thought to be responsible for the cytotoxic effect. In addition, the invention compounds that are photoactivated by using appropriate excitation wavelengths may fluoresce. This fluorescence can be used to localize the tumor or other target tissue.

In general, the same wavelength range can be used for inducing cytotoxicity as for exciting fluorescence; if fluorescence is to be directly observed, however, it is advantageous to use appreciably shorter wavelengths so that the excitation radiation does not interfere with the observation of the fluorescence.

The radiation for mediating cytotoxicity or fluorescence emission can be supplied by standard sources of visible radiation, including incandescent or fluorescent light sources using suitable filters, or can be supplied by photodiodes, such as light-emitting diodes at a narrow wavelength range. In addition, laser light is often convenient for the in situ delivery of light to the localized photosensitizer of the invention. Thus, among the sources that have been used in photodynamic therapy and diagnosis in general are quartz, halogen and arc lamp sources, monochromatic light from a fixed wavelength, gold vapor, tunable argon-pump dye laser or other wavelength-specific lasers, and standard visible light sources in general.

Particularly preferred in the therapeutic and diagnostic practice of the invention are light-emitting diodes (LEDs) which produce sufficient radiation to activate the photosensitizing compounds and are relatively inexpensive, small in size, and do not require special utilities for operation. The relatively broad-band light generated from LEDs, as compared to the single wavelength generated by laser radiation, allows advantage to be taken of the broad wavelength absorption of the invention compounds.

Most LEDs have emission bands of about 20-40 nm and can operate from the green (500 nm) to the near infrared. Typical lasers used in photodynamic therapy and diagnosis involving the compounds of the invention include metal vapor or dye lasers, such as the argon-pumped dye laser or copper vapor-pumped dye laser or Nd:YAG-pumped dye laser, among others. In use, the laser system generally consists of 2-3 separate lasers arranged serially to achieve the desired output wavelength and optical power. Lasers are less efficient in conversion of electrical to optical energy than LEDs—for the argon laser values in the range of 0.01-0.25% are typical—whereas LEDs have electrical-to-light conversion efficiencies of about 8%. LEDs also have longer lifetimes as compared to the 2,000-3,000 hours available from typical argon lasers.

Any suitable light source can be used for irradiation of the tissue to effect cytotoxicity or excite fluorescence in those tissues in which the invention compounds reside. However, light-emitting diodes are preferred.

It is also feasible to generate the photoactivating light using a system which produces light by virtue of a chemical reaction. In these systems, a chemical transition which liberates energy sufficient to excite visible wavelength emissions from a suitable compound is responsible for the radiation. A chemiluminescent system (CLS) wherein a substituted oxamide reacts with hydrogen peroxide in the presence of a sulfonated rubene to produce an intense yellow-red light lasting 10-20 minutes was reported to be useful as an irradiation source in photodynamic therapy.

In addition to irradiation for excitation of the invention compounds for therapy, additional forms of irradiation which can independently destroy the tissue irradiated can be used to supplement the effect of the photodynamic therapy per se. Thus, the therapeutic methods of the invention can employ a variety of irradiation means for activation of the photosensitizer, alone or in combination with additional radiation designed for direct treatment of tumor, said direct treatment radiation typically including X-rays, microwave radiation, and the use of additional photochemicals as chemiluminescent or fluorescent radiation transfer materials.

In addition to additional irradiation, the photodynamic treatment can be accompanied by adjuvant therapy using approaches such as surgery, radiation and chemotherapy. Also, PDT potentiators, such as glucose, which depresses tumor pH and results in greater accumulation of the photosensitizer and thus more effective cytotoxicity, can be used. Other adjuvant treatments which can be used along with photodynamic therapy include the use of protective agents such as cadmium chloride for topical application, misonidazole (MISO), or ethanidazole for protection against direct cellular phototoxicity of intermediate oxygen concentration, or antiinflammatories such as ibuprofen and ASA as protective agents.

Typical of the indications targeted for photodynamic treatment include in vivo treatment for destruction of tumor tissue in solid tumors and for dissolution of plaques in blood vessels; prevention of restenosis; and treatment of topical conditions such as acne; athlete's foot; warts; papilloma, including venereal, laryngeal and dermal; unwanted tissue in general, such as hair follicles or fat deposits; port wine stains; hypervascularization, including varicose veins and spider veins; and psoriasis. Other indications include the systemic treatment of tumors and neoplastic tissues, such as malignancies that occur in brain, face, mouth, throat, lung, gastric, rectal, prostate, ovarian, breast, skin (basal, melanoma), bone, blood, hematopoietic, lymph, bronchial, cervical, esophageal or colon tissues and Kaposi's Sarcoma. The invention photosensitizer complexes also are useful for treatment of biological products (such as blood for transfusion) for infectious agents, since the presence of a membrane in such agents promotes the accumulation of the drug.

In particular, the invention photosensitizer complexes are useful for eradicating infectious agents, in vivo or ex vivo, including viral contaminants often found in donated blood or blood products. Such infectious and viral contaminants include, for example, bacterial, fungal or parasitic infection, hepatitis B, hepatitis A or hepatitis C virus, human immunodeficiency virus (HIV), cytomegalovirus (CMV), and Epstein-Barr virus. Vesicular stomatitis virus (VSV), while not usually found in human blood, behaves in a similar manner in response to the photodynamic treatment. In addition, parasites such as *Trypanosomes* or *Plasmodium* are susceptible targets. All of the foregoing infectious agents can be eradicated by the methods of the invention both in vivo and ex vivo.

For use in in vivo treatment or diagnosis of atherosclerotic plaques or malignancies or infections treated systemically, the photosensitizer complexes are typically administered by injection, and permitted sufficient time to home to the atherosclerotic plaques, malignancies or infective agents, usually about 30 minutes to 3 hours. The plaques or malignancies are then subjected to irradiation for therapeutic effect to dissolve the plaque or destroy the tumor cells.

Injection may be intravenous, subcutaneous, intramuscular, or even intraperitoneal. Injectables can be prepared in conventional forms, either as liquid solutions or suspensions, solid form suitable for solution or suspension in liquid prior to injection, or as emulsions. Suitable excipients are, for example, water, saline, dextrose, glycerol and the like. Of course, these compositions may also contain minor amounts of nontoxic, auxiliary substances such as wetting or emulsifying agents, pH buffering agents and so forth.

If treatment is to be localized, such as for the treatment of superficial tumors or skin disorders, the photosensitizer complexes may be topically administered using standard topical compositions involving lotions, suspension, or pastes. The topical formulations may contain typical excipients and are in the form of liquids, creams, gels or ointments.

In addition to in vivo use, the photosensitizer complexes of the invention can be used in the treatment of materials in vitro to destroy harmful viruses or infectious agents. For example, blood plasma or blood which is to be used for transfusion or banked for future transfusion can be treated with the photosensitizer complexes of the invention and irradiated to effect sterilization. In addition, biological products such as Factor VIII which are prepared from biological fluids can be irradiated in the presence of the photosensitizer complexes of the invention to destroy contaminants. The biological sample is incubated with the photosensitizer complex for one to several hours, usually at room temperature, along with exposure to light. The biological fluid in the presence of photosensitizer complex is irradiated using an appropriate light source, such as a tungsten light bulb emitting over the range of the visible spectrum with light intensity of about 5-10 mW/cm$^2$, or LEDs with emission bands in the appropriate range for absorption by the photosensitizer.

EXAMPLES

Methods and Materials

Silver nitrate (99.9%), sodium hydroxide (99.996%), ammonium hydroxide (30%), D-glucose and premium quality Silane-Prep™ glass slides (75×25 mm) were obtained from Sigma. The singlet oxygen Green sensor reagent (GR), was obtained from molecular probes (Invitrogen) and is highly selective for $^1O_2$. In the presence of singlet oxygen, it emits a green fluorescence (excitation/emission 504/525 nm). (24) Rose Bengal, Acridine, Chloroquine, Indomethacin, Riboflavin, Naproxen, Chloropromazine and Quinedine were also obtained from Sigma. All chemicals were used as received.

Preparation of Silver Island Films (SiFs): Silver Island Films (SiFs) were prepared according to previously published procedures (30).

Preparation of Sandwich Format Samples: A solution of 500 μL of photosensitizer (0.1 mM) in water and a solution of 500 μL GR (4.5 mM) (also in water) was sandwiched between the glass slides and SiFs, respectively. The glass/SiFs surfaces were exposed to a Mercury lamp (UV-light, 365 nm, 100 W) for 2 minutes for singlet oxygen generation and also used for UV irradiation measurements.

Absorption and Fluorescence Measurements: Absorbance spectra were taken using a Varian Cary 50 UV-Vis Spectrophotometer. Fluorescence emission was collected at 45 degrees relative to the excitation angle through a long pass filter, using a Fiber Optic Spectrometer (HD2000) from Ocean Optics, Inc. A 473 nm laser line was used for excitation.

Singlet Oxygen Yield Enhancement Factor Measurements: On silver island films the enhancement factor was calculated from:

$$GR_{MEF,before} = \frac{\int_0^\infty GR_{SiF,before}\, d\lambda}{\int_0^\infty GR_{GL,before}\, d\lambda} \quad (1)$$

whereby $$\int_0^\infty GR_{SiF,before}\, d\lambda \text{ and } \int_0^\infty GR_{GL,before}\, d\lambda$$

are the integrated spectra (FIG. 2A) for the green photosensitizer (GR), before exposure to UV light on silver island films (SiF) and glass substrates (GL), respectively. The calculation of the MEO (metal enhanced singlet oxygen yield) of the photosensitizer is as follows $$^1O_{2,MEO} = \frac{\int_0^\infty GR_{SiF,after}\, d\lambda - \int_0^\infty RB_{\lambda_n,SiF,after}\, d\lambda}{GR_{MEF,before}(\int_0^\infty GR_{GL,after}\, d\lambda - \int_0^\infty RB_{GL,after}\, d\lambda)} \quad (2)$$

whereby $$\int_0^\infty RB_{SiF,after}\, d\lambda$$

and $$\int_0^\infty RB_{GL,after}\, d\lambda$$

and $$\int_0^\infty GR_{SiF,after}\, d\lambda$$

-continued $$\int_0^\infty GR_{GL,after}\, d\lambda$$

are the integrated spectra for Rose Bengal (RB) and the photosensitizer (GR) after exposure to UV light (FIG. 2B) on silver island films (SiF) and glass substrates (GL), respectively.

Finite difference time domain (FDTD) simulations: The FDTD method was employed here to determine the electric field intensities and distributions at the surface of a 100 nm silver nanoparticle in a Total Field Scattered Field. These results were compared with Mie Theory and previously published reports to verify the accuracy of the model.(18) Total field scattered-field sources were used to divide the computation area or volume into total field (incident plus scattered field) and scattered field only regions.(32) The incident field is defined as a plane wave with a wave vector that is normal to the injection surface and the scattered and total field are monitored during the simulation such that the total or scattered transmission can be measured. Using Lumerical FDTD Solution software (Canada), the simulation region is set to 700×700×700 nm$^3$ with a mesh accuracy of 6. To minimize simulation times and maximize the resolution of field enhancement regions around the metal sphere, a mesh override region was set to 1 nm around the 100 nm Ag sphere. The overall simulation time was set to 200 ns and calculated over a frequency range from 300-600 nm, whereby a plasma model was used to represent the properties of the silver nanoparticle in the range from 300 nm to 600 nm.

Example 1

Determining Properties of ME $^1O_2$

FDTD methods were used to demonstrate direct evidence for the relationship of electric field enhancements around nanoparticles and the increase in triplet yields for a photosensitizer and the subsequent increase in singlet oxygen generation. Several photosensitizers were studied wherein each photosensitizer had singlet oxygen yields ranging from 0.08 to 1.00 and were sandwiched between silver island films (SiFs) for Metal-Enhanced singlet oxygen generation (ME$^1O_2$). Notably, an inverse relationship between singlet oxygen enhancement factor and the free-space singlet oxygen quantum yield was observed. In addition, it was observed that there was a distance dependence for the generation of ME$^1O_2$ from photosensitizers on SiFs substrates using SiOx layers 0.5, 2, 5, 10 nm thick. These observations are consistent with numerous distance dependence measurements for MEF and MEP themselves.

Since Rose Bengal is a commonly used photosensitizer with high singlet oxygen yield (0.76), it was selected to demonstrate the properties of metal enhanced singlet oxygen generation.(22) Notably, although there are several singlet oxygen detection reagents available (23, 24), green sensor (GR) was chosen because it is highly selective for singlet oxygen. (24) The solutions of GR and RB have well-separated fluorescence peaks at 525 nm (FIG. 2A) and 588 nm (FIG. 2B). Thus, the green sensor (GR) detects singlet oxygen, while Rose Bengal is the photosensitizer that triggers singlet oxygen generation, due to a triplet interaction with ground-state molecular oxygen. Without UV irradiation (sensitization) a green fluorescence emission peak at 525 nm for the GR singlet oxygen sensor on glass (FIG. 2A) was observed. This emission peak was attributed to background solution singlet oxygen and emission of the sensor dye.(25) Due to the MEF effect,(9) the fluorescence emission peak of GR is enhanced on SiFs as shown in FIG. 2A, which was corrected for in the calculations used for showing enhanced singlet oxygen yields (MEF Factor, Equation 1).

After exposure to UV light, the fluorescence emission intensity of GR on SiFs (FIG. 2D) at 525 nm is ~3.3 times larger than GR emission on glass (FIG. 2C). This increased intensity suggests that more singlet oxygen was generated from the Rose Bengal system on SiFs. The photographs, as shown in FIGS. 2C and D, further validate the difference of GR fluorescence emission intensity on glass and SiFs, respectively. As noted, on glass, the photographs of GR/RB solutions of FIG. 2C before exposure to UV light are visually brighter after exposure to UV light, which reflects an increase in singlet oxygen yield. On SiFs, shown in FIG. 2D, this increased brightness of the solution is more pronounced further suggesting that the presence of the Ag nanoparticles facilitates increased singlet oxygen generation.

Since SiFs are compared to a glass substrate for the production of enhanced singlet oxygen generation, it is important to discuss the similarities in the surface features of these substrate materials. As described in the previously published procedure (10), SiFs are deposited onto the same glass substrate (used for the comparison of singlet oxygen generation) as particles with a diameter in the order of 30 nm and with a surface coverage of ≈40%. Thus, the comparison of a blank glass substrate with the same glass substrate containing SiFs for singlet oxygen generation is deemed appropriate.

To confirm that the observed signal enhancement in the presence of SiFs is due to an increase in singlet oxygen yield due to silver, the oxygen supply was varied. After extensive purging the RB and GR solution with $N_2$ and subsequent exposure to UV irradiation, it was observed that the amplitude of the peak at 525 nm does not change in the cuvette (FIG. 2E) or on SiFs (FIG. 2F). As expected, these results indicate that no singlet oxygen was generated. However, after purging the mixture of RB and GR solution with oxygen and subsequent exposure to UV irradiation (sensitization), a sharp increase in the GR fluorescence peak intensity from SiFs was observed due to singlet oxygen generation (FIG. 2G). A mixture of RB and GR solution on a continuous silver strip was also studied. No enhanced singlet oxygen generation was observed on the continuous silver strip as shown in FIG. 2H, since surface plasmons cannot be generated in a continuous strip of metal (from the air side) but can be generated in non-continuous particulate silver island films.

Figure 3:
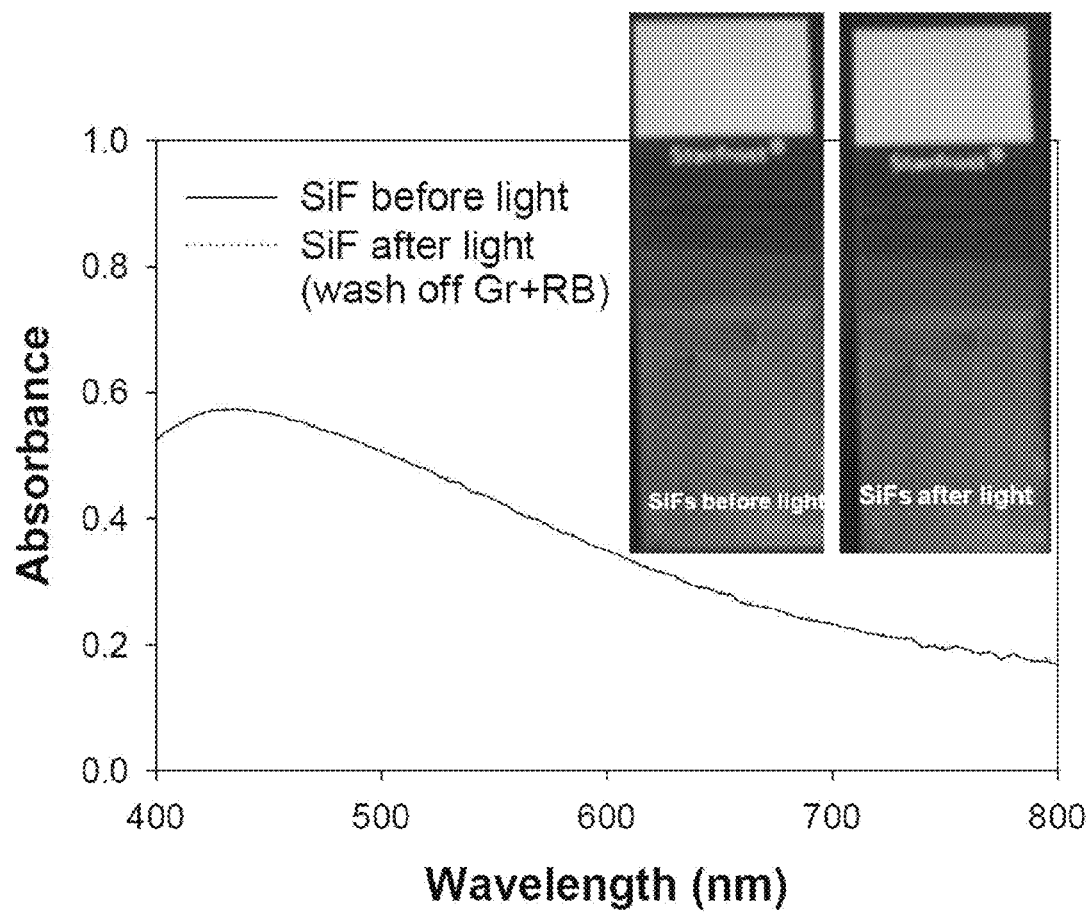
FIG. 3 shows the absorption spectra of SiFs before and after light showing no effect on the silvered surface by $^1O_2$. SiFs—Silver island Films. Light—UV exposure.

In order to demonstrate that the SiFs are unaffected by $^1O_2$ or UV irradiation, the absorption spectra of SiFs before UV irradiation and SiFs previously coated was compared with the GR/RB mixture and exposed to UV irradiation (FIG. 3). No change was observed in the plasmon absorbance spectra for the SiFs samples before and after UV irradiation. Subsequently, Thus, it was understood that no structural changes to the SiFs or indeed surface plasmon oscillation would account for increased absorption or enhanced triplet generation.

To demonstrate that the present described approach for enhancing Triplet yields is not limited to solutions of Rose Bengal, many other photosensitizers were tested to show the enhancement of singlet oxygen quantum yields wherein the photosensitizers had singlet oxygen yield varying from 0.08 to 1.00.

Figure 4:
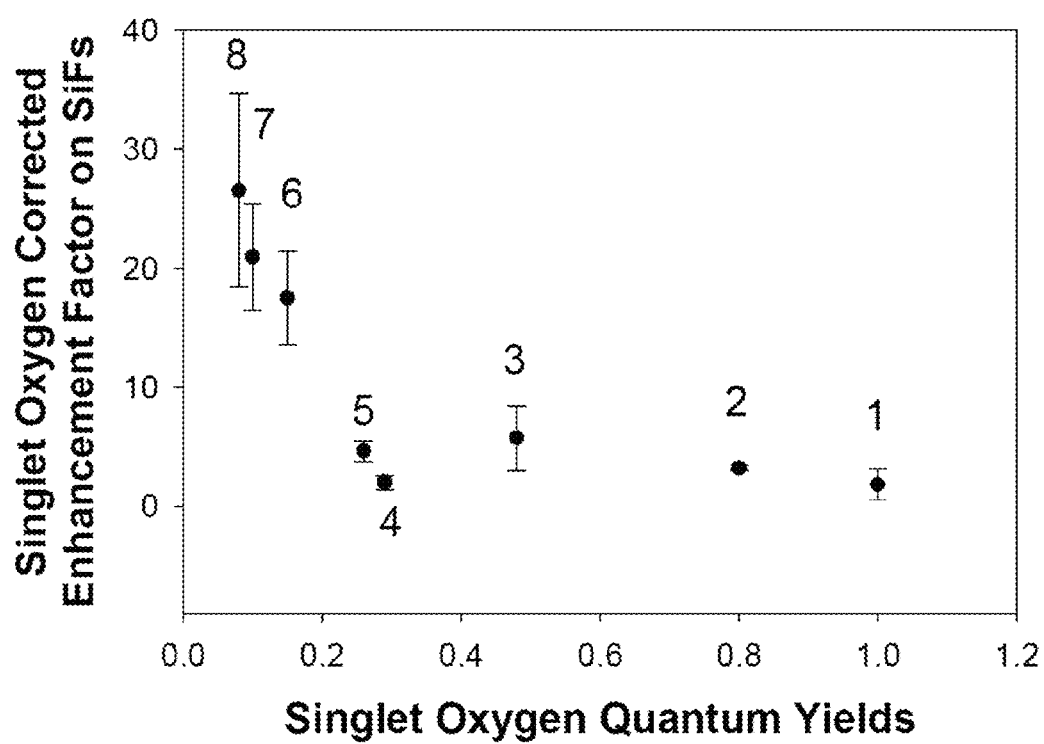
FIG. 4 shows the singlet Oxygen Corrected Enhancement Factor on SiFs versus free—space Singlet Oxygen Quantum Yield. (1. Acridine 2. Rose Bengal 3. Chloroquine 4. Indomethacin 5. Riboflavin 6. Naproxen 7. Chlorpromazine 8. Quinidine). Error bars are based on the standard deviation of 3 spectral measurements.

In order to calculate the singlet oxygen enhancement of these photosensitizers, the MEF factor of the photosensitizer was calculated. The MEF factor of the photosensitizer, $GR_{MEF,before}$, on silver island films is calculated by:

$$GR_{MEF,before} = \frac{\int_0^\infty GR_{SiF,before} \, d\lambda}{\int_0^\infty GR_{GL,before} \, d\lambda} \quad (3)$$

whereby $$\int_0^\infty GR_{SiF,before} \, d\lambda \text{ and } \int_0^\infty GR_{GL,before} \, d\lambda$$

are the integrated spectra (FIG. 2C) for the green sensor dye (GR), before exposure to UV light on silver island films (SiF) and glass substrates (GL), respectively. The calculation of the MEO (metal enhanced singlet oxygen yield) of the photosensitizer is as follows $$^1O_{2,MEO} = \frac{\int_0^\infty (GR, RB)_{SiF,after} \, d\lambda - \int_0^\infty RB_{\lambda_n, SiF,after} \, d\lambda}{GR_{MEF,before}(\int_0^\infty (GR, RB)_{GL,after} \, d\lambda - \int_0^\infty RB_{GL,after} \, d\lambda)} \quad (4)$$

whereby $$\int_0^\infty RB_{SiF,after} \, d\lambda$$

and $$\int_0^\infty RB_{GL,after} \, d\lambda$$

and $$\int_0^\infty (GR, RB)_{SiF,after} \, d\lambda$$

and $$\int_0^\infty (GR, RB)_{GL,after} \, d\lambda$$

are the integrated spectra for Rose Bengal (RB) and the mixture of photosensitizer (GR) with Rose Bengal (RB) after exposure to UV light on silver island films (SiF) and glass substrates (GL), respectively (FIG. 2D). As shown in FIG. 4, the enhancement factor is 26.6±8.13 for Quinidine, which has a free-space singlet oxygen quantum yield of 0.08. In contrast, for Acridine which has a high singlet oxygen yield of 1.00, the enhancement factor is 1.83±1.35. Interestingly, the enhanced singlet oxygen yield factor appears to be inversely proportionally to free-space singlet oxygen yield. This finding is consistent with the MEF enhancement factor for fluorophores and (relative intensities in the presence and absence of metal for the fluorophores) increases as the free-space quantum yield ($Q_0$) decreases.(27)

In order to determine the distance dependence of $ME^1O_2$, SiOx layers of 0.5, 2, 5 and 10 nm thickness were vapor deposited on SiFs, as shown in FIG. 5D. It was observed that the amplitude of the emission spectra of GR and RB solution on SiFs varied with different thickness of SiOx, as shown in FIG. 5C. The singlet oxygen enhancement factor of GR and RB solution on SiFs was 2.0-fold for 0.5 nm SiOx coatings, 1.5-fold for 2.0 nm SiOx, 1.3-fold enhancement for 5 nm SiOx coatings, and no enhancement on 10 nm SiOx was observed.

To subsequently correlate the electric field enhancements of the incident excitation radiation on the SiFs (29) with the distance dependence of the RB photosensitizer from the metal, FDTD calculations were used to simulate the electric field enhancements of a 330 nm source around a 100 nm silver nanoparticle as shown in FIGS. 5A and B. It was observed that a non-linear relationship exists between the experimentally calculated distance dependent enhancement of singlet oxygen yields for SiOx films deposited on silver island films and the simulated electric field enhancements, as shown in FIG. 5C.

Example 2

Figure 7:
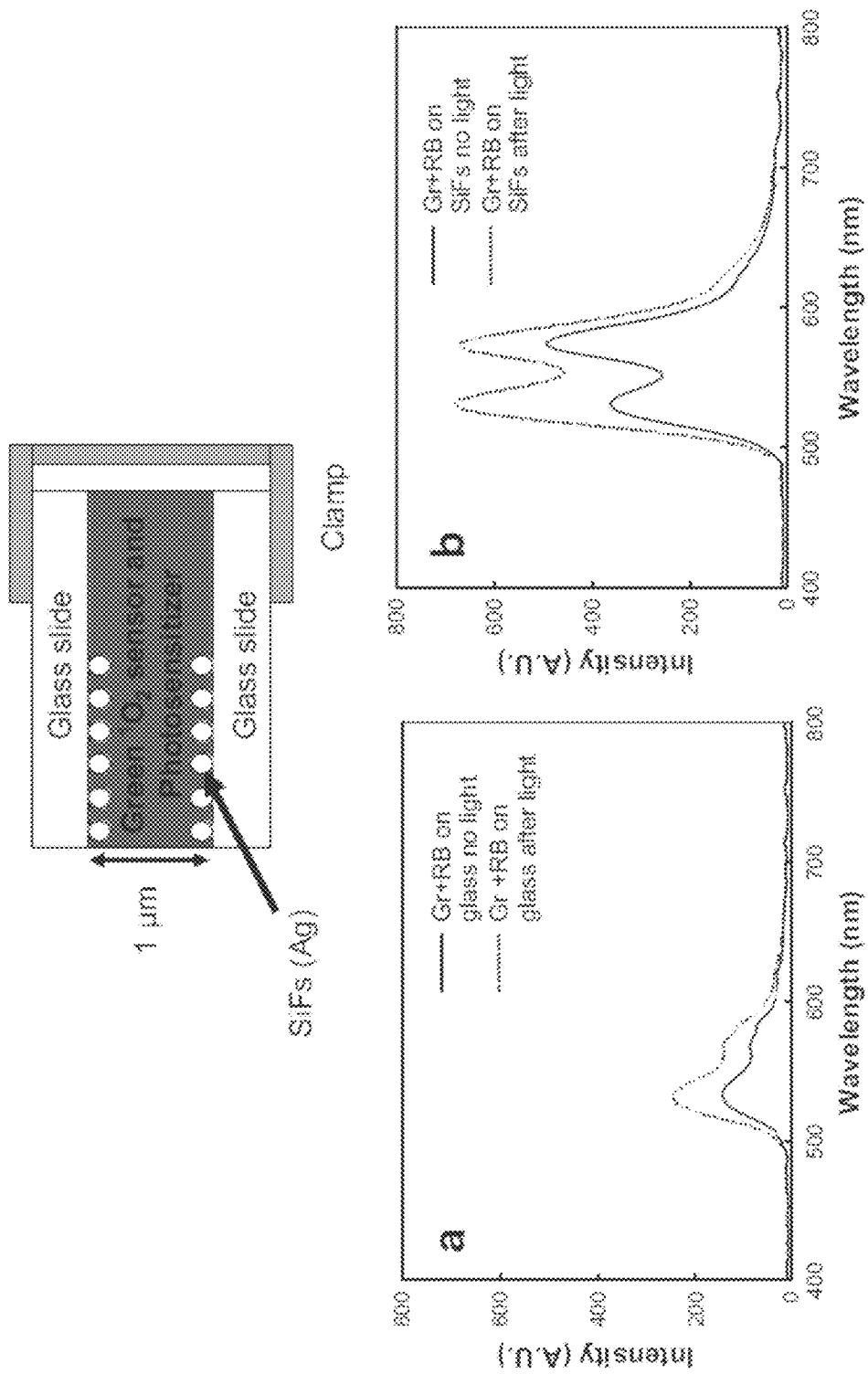
FIG. 7 is a schematic representation of the sample geometry (Top), and fluorescence emission spectra (Bottom) of a mixture of the green sensor (GR) and Rose Bengal (RB) on glass a, mixture on SiFs b, before and after light exposure (2 min) at room temperature. Light source is 100 W mercury lamp. $\lambda_{ex}$=473 nm. The spectra have been corrected for the MEF effect on the GR emission.

A solution of 500 µl of Rose Bengal (0.1 mM) in ethanol and a solution of 500 µl GR (4.5 mM) also in ethanol was dropped in a sandwich format between the glass slides and the silver island films (SiFs), respectively. FIG. 7-Top shows the experimental sandwich sample geometry. The glass/SiFs surfaces were exposed to UV-light (365 nm (100 W)) for 2 min for singlet oxygen generation, with the green sensor dye fluorescence collected at 45° to the excitation through a long pass filter, using a Fiber Optic Spectrometer (HD2000) from Ocean Optics, Inc.

FIG. 7—Bottom shows the fluorescence emission spectra of a mixture of GR and Rose Bengal solutions on glass and SiFs, before and after UV light exposure. While the peak at 588 nm is the Rose Bengal fluorescence emission and not related with singlet oxygen (12), the peak at 525 nm originates from the GR sensor dye emission and directly correlates with singlet oxygen yield. It can be seen that the fluorescence emission intensity at 525 nm is increased after UV light exposure, which is indicative of singlet oxygen generation. On SiFs, the fluorescence intensity at 525 nm was increased ≈3.3 fold, as compared to that on glass. The increased intensity signifies that more singlet oxygen was generated from the Silver-Rose Bengal system after light exposure. The spectra are corrected for the increased intensity of the GR sensor by the MEF effect, so that the ME $^1O_2$ can be solely observed.

It is believed that the mechanism of singlet oxygen generation from the photo-sensitizer is an energy transfer process during a collision of the excited lumophore with $^3O_2$. Since the lifetime of the triplet excited $T_1$ state (micro or millisecond range) is much longer than that of the singlet excited $S_1$ state (nanosecond), it is long enough for the triplet excited state to react with (ground-state triplet oxygen) $^3O_2$ to form $^1O_2$, in essence competing with the more favorable phosphorescence emission. At first consideration one may be surprised by the presence of both enhanced MEP(12) and $ME^1O_2$ in the same system, as both processes are competitive and provide a route for the deactivation of electronic excited triplet states.

With regard to singlet oxygen generation, it should also be noted that the true metal-enhanced singlet oxygen enhancement factor is ≈25 times larger than previously observed.

This is because the ME $^1O_2$ phenomenon, like MEF and MEP, is through-space, with an interaction distance of less than 20 nm. Thus, with a sample thickness of ≈1 µm, only 4% of the sample is within the plasmon enhancement region (See FIG. 7—Top). As such, in addition to close proximity nanostructures, other factors such as temperature, surface roughness and indeed shape of SiFs or nanostructures can also influence the extent of $ME^1O_2$ formed, effectively providing tools to manipulate the $ME^1O_2$ yield, and to some degree, therefore PDT therapy.

Figure 8:
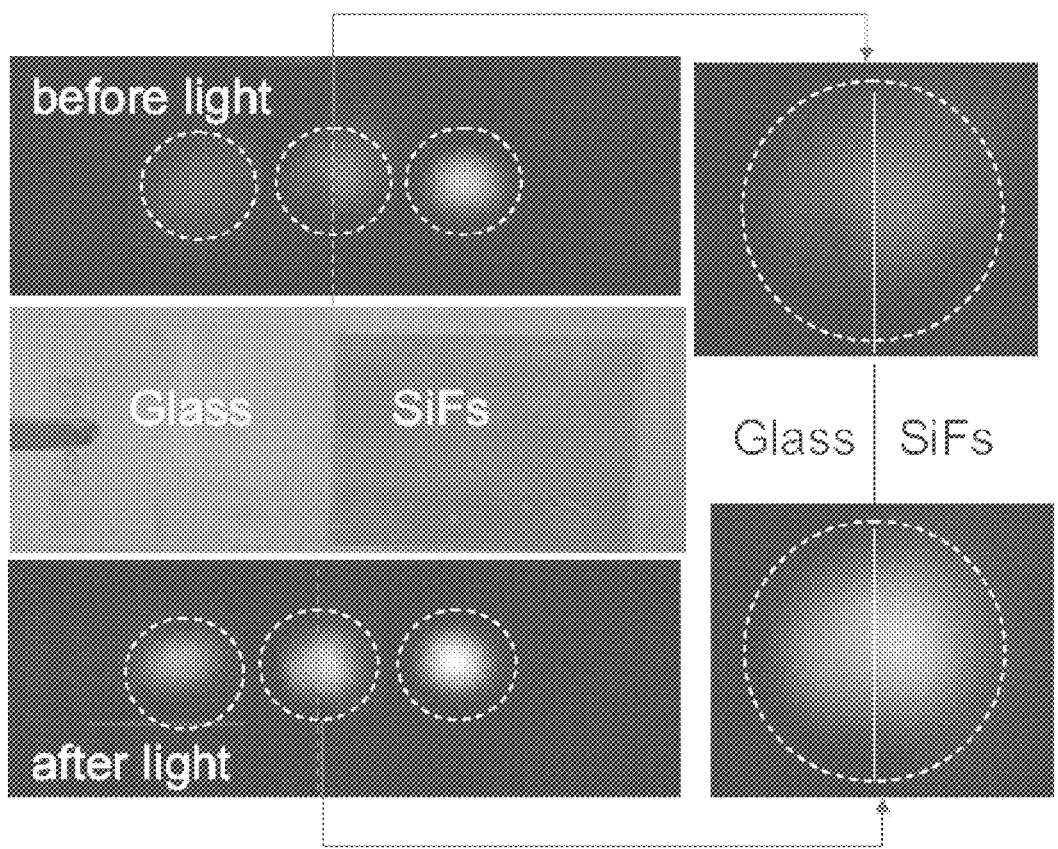
FIG. 8 shows emissions of Green $^1O_2$ sensor (GR) and Rose Bengal (RB) from glass and SiFs, before and after 2 min light exposure. Light exposure source was a 100 W mercury lamp. $\lambda_{ex}$=473 nm. SiFs—Silver Island Films. Note! As the excitation (circles) spots are moved from the glass to the SiFs, more emission is observed. The right hand side photographs show the sample half glass and half SiFs.

It is interesting to visually observe the enhanced $ME^1O_2$ yield in the presence of the green sensor, as shown in FIG. 8.

It can be seen that the GR fluorescence emission intensity on glass before light exposure is dim. However on SiFs before light exposure it looks brighter than on glass due to MEF. In contrast, after light exposure, the GR fluorescence emission on glass was easily observed. This indicates the generation of singlet oxygen after the exposure of RB to UV radiation. Importantly, the GR fluorescence emission was far more intense on SiFs after light exposure, indicating that more singlet oxygen is generated on SiFs than on the glass slide.

Example 3

Superoxide Generation

SiFs were deposited on glass slides as previously published and described above. DHE, a well known superoxide probe, is highly selective for superoxide and in the presence of superoxide, it emits an orange fluorescence (excitation/emission: 473 nm/586 nm). A 300 µl solution of the photosensitizer, acridine (50 µM in ethanol) and DHE (0.845 mM in ethanol), was trapped in a sandwich format between the glass and the silver island films, as shown in the FIG. 9, insert. A control sample, which uses the same glass slides but with no silver deposits, was used to determine the extent of the plasmon-enhanced superoxide generation. Glass slides were deemed appropriate due to the long wavelength absorption of the acridine photosensitizer and DHE probe (430 and 473 nm, respectively) as compared to the intrinsic absorption by glass (<340 nm). $SiO_2$ coatings, for distance dependence measurements, were deposited using thermal vapor deposition (Edwards Auto 380), where the $SiO_2$ layers were shown not to perturb the plasmon absorption spectra of the SiFs (data not shown).

Figure 9:
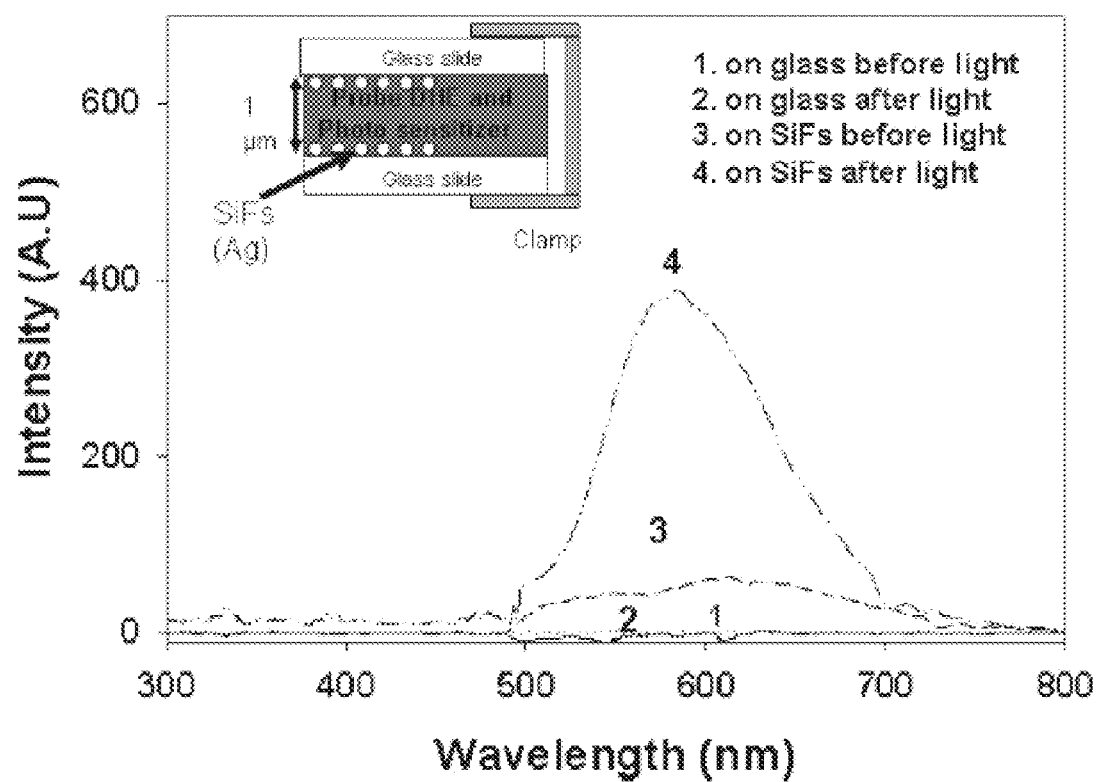
FIG. 9 is a schematic representation of the sample geometry (insert) and fluorescence emission spectra of a mixture of the DHE probe and acridine on glass and on SiFs, before and after light exposure (2 min) at room temperature. Light source was a 100 W mercury lamp. $\lambda_{ex}$=473 nm. DHE—dihydroethidium. SiFs—silver island films.

FIG. 9 shows the fluorescence emission spectra of a mixture of DHE and acridine solutions on glass and SiFs, before and after UV light exposure. On glass, no fluorescence was detected both before and after light exposure, where exposure (from 10 cm away for 2 min) with a 100 W mercury lamp was used with the acridine photosensitizer for the generation of superoxide. This suggests that too little superoxide was generated to be detected in the glass sandwich using the DHE probe. However, on SiFs before exposure, one broad peak at 595 nm was observed, which is attributed to the amplified fluorescence peak of DHE. This peak becomes apparent on the SiFs but is not visible on the glass control sample due to the MEF effect, which has been previously shown to significantly enhance the emission intensity for nearly every fluorophore tested to date.(30) After UV light exposure, a significant increase in the fluorescence emission of the DHE probe at 595 nm was evident from SiFs, which strongly indicates enhanced superoxide generation as compared to the glass control sample, which contains no silver nanostructures (Note: the MEF effect on the DHE probe in the absence of acridine has been corrected for).

Figure 10:
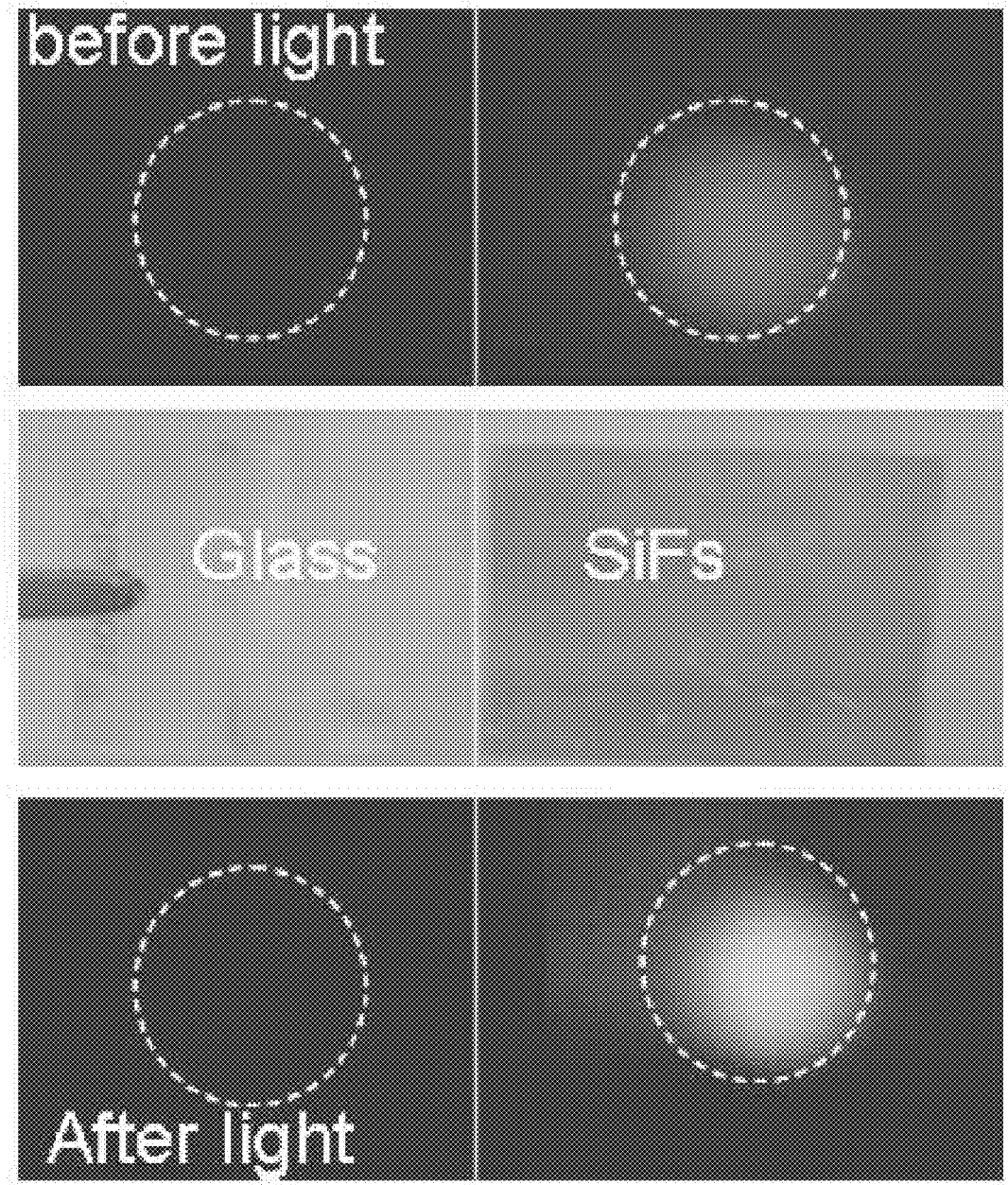
FIG. 10 shows emissions of DHE and acridine from glass and SiFs, before and after 2 min light exposure (sensitization). Light exposure source was a 100 W mercury lamp. $\lambda_{ex}$=473 nm. SiFs—silver island films.

These enhancements can also be evidenced visually from FIG. 10 photographs. On glass, the DHE fluorescence emission was not observed before and after exposure, FIG. 10 top left and bottom left, respectively. However, on SiFs, the DHE fluorescence emission was much more intense after light exposure in the presence of the acridine photosensitizer, indicating that more superoxide anion radical is generated on SiFs than on the glass slide, see the top right panel and bottom right panel of FIG. 10. It is interesting to note that the photographs were taken through an emission filter and the intensities observed are not due to backscattering of the excitation light by silver. The middle panel shows a photograph of the silver island films, coated on only half of the glass slide.

It was again surprising that the presence of metal-enhanced fluorescence/phosphorescence and metal-enhanced superoxide anion radical generation occurred in the same system, as these processes are effectively competitive and ultimately will provide a route for deactivation of electronic excited states. However, as discussed above, simultaneous photophysical mechanisms can be present within the same system when enhanced absorption effects of the photosensitizer near to silver are present (i.e., an enhanced excitation rate). In this case, enhanced absorption of acridine near-to the plasmon resonant particles facilitates MEF, MEP, ME $^1O_2$, and also metal-enhanced superoxide generation simultaneously within the same system.

Figure 11:
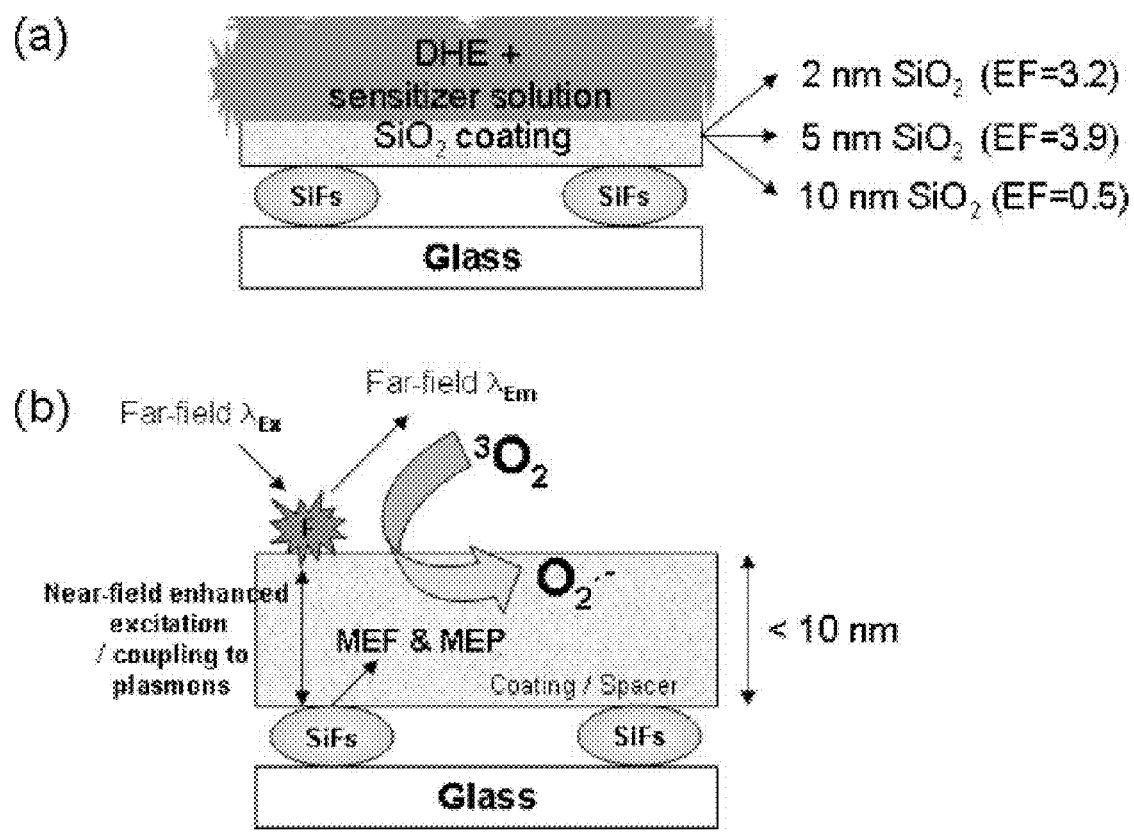
FIG. 11 shows a sample architecture for the distance dependence of metal-enhanced superoxide generation (top), and graphical representation of the interpretation of metal-enhanced superoxide generation with an enhanced and distance dependent excitation rate (bottom). F—fluorophore, MEF—metal-enhanced fluorescence, MEP—metal-enhanced phosphorescence, SiFs—silver island films. EF—enhancement factor=$I_{silver}/I_{glass}$.

The generation of superoxide was investigated to determine if the effect would be influenced by the distance of both the sensitizer and DHE probe from the metallic surface, in an analogous manner to MEF. A $SiO_2$ coatings was deposited by thermal vapor deposition on the surface of the SiFs, effectively distancing the probes from the silvered surface when in a sandwich geometry as shown in FIG. 11. It was determined that close proximity to silver, that being 2 nm, results in only modest enhancements of superoxide as compared to the glass control sample. For 10 nm $SiO_2$ coatings the enhancement factor was the smallest, that being, approximately 0.5. However, for the 5 nm $SiO_2$ coating the system yielded an approximately four-fold enhancement in superoxide generation as compared to the glass slide control sample.

It appears that the enhanced absorption component of the sensitizer near to silver is also distance dependent, with a maximum value near 5 nm. Thus, superoxide anion radical is generated near to silver surfaces in a distance dependent manner, analogous to reports of metal-enhanced fluorescence. This suggests that the distance dependence of the excitation rate of the acridine sensitizer manifests itself in an increased triplet and therefore superoxide anion radical yield.

REFERENCES

The contents of all references set forth below are incorporated by reference herein for all purposes.
1. Demidova, T. N. & Hamblin, M. R. (2004) *International Journal of Immunopathology and Pharmacology* 17, 245-254.
2. Brown, S. B., Brown, E. A., & Walker, I. (2004) *Lancet Oncology* 5, 497-508.
3. Kendall, C. A. & Morton, C. A. (2003) *Technology in Cancer Research & Treatment* 2, 283-288.
4. Dougherty, T. J. (2002) *Journal of Clinical Laser Medicine & Surgery* 20, 3-7.
5. Jarvi, M. T., Niedre, M. J., Patterson, M. S., & Wilson, B. C. (2006) *Photochemistry and Photobiology* 82, 1198-1210.
6. Moan, J., Peng, Q., Sorensen, R., Iani, V., & Nesland, J. M. (1998) *Endoscopy* 30, 387-391.
7. Bauer, J., Chen, K. H., Hiltbunner, A., Wehrli, E., Eugster, M., Schnell, D., & Kessler, F. (2000) *Nature* 403, 203-207.
8. Thompson, M. S., Johansson, A., Johansson, T., Andersson-Engels, S., Svanberg, S., Bendsoe, N., & Svanberg, K. (2005) *Applied Optics* 44, 4023-4031.
9. Geddes, C. D. & Lakowicz, J. R. (2002) *Journal of Fluorescence* 12, 121-129.
10. Aslan, K., Leonenko, Z., Lakowicz, J. R., & Geddes, C. D. (2005) *Journal of Fluorescence* 15, 643-654.
11. Zhang, Y., Aslan, K., Malyn, S. N., & Geddes, C. D. (2006) *Chemical Physics Letters* 427, 432-437.

12. Zhang, Y., Aslan, K., Previte, M. J. R., Malyn, S. N., & Geddes, C. D. (2006) Journal of Physical Chemistry B 110, 25108-25114.
13. Zhang, Y. X., Aslan, K., Previte, M. J. R., & Geddes, C. D. (2007) *Journal of Fluorescence* 17, 345-349.
14. Barber, P. W., Chang, R. K., & Massoudi, H. (1983) *Physical Review B* 27, 7251-7261.
15. Yang, W. H., Schatz, G. C., & Vanduyne, R. P. (1995) *Journal of Chemical Physics* 103, 869-875.
16. Yee, K. S. & Chen, J. S. (1997) *Ieee Transactions on Antennas and Propagation* 45, 921-925.
17. Kelly, K. L., Coronado, E., Zhao, L. L., & Schatz, G. C. (2003) *Journal of Physical Chemistry B* 107, 668-677.
18. Challener, W. A., Sendur, I. K., & Peng, C. (2003) *Opt. Express* 11, 3160-3170.
19. Yee, K. S. (1966) Antennas and Propagation, *IEEE Transactions* 14, 302-307.
20. Foteinopoulou, S., Vigneron, J. P., & Vandenbem, C. (2007) *Optics Express* 15, 4253-4267.
21. Hao, E. & Schatz, G. C. (2004) *Journal of Chemical Physics* 120, 357-366.
22. Redmond, R. W. & Gamlin, J. N. (1999) *Photochemistry and Photobiology* 70, 391-475.
23. Hideg, E., Barta, C., Kalai, T., Vass, I., Hideg, K., & Asada, K. (2002) *Plant & cell physiology* 43, 1154-1164.
24. Flors, C., Fryer, M. J., Waring, J., Reeder, B., Bechtold, U., Mullineaux, P. M., Nonell, S., Wilson, M. T., & Baker, N. R. (2006) *Journal of Experimental Botany* 57, 1725-1734.
25. Stiel, H., Teuchner, K., Paul, A., Leupold, D., & Kochevar, I. E. (1996) *Journal of Photochemistry and Photobiology B: Biology* 33, 245-254.
26. Zhang, Y. X., Aslan, K., Previte, M. J. R., Malyn, S. N., & Geddes, C. D. (2006) *Journal of Physical Chemistry B* 110, 25108-25114.
27. Lakowicz, J. R. (1999) Principles of Fluorescence Spectroscopy (Kluwer Academic, New York).
28. Asian K, Previte M J R, Zhang Y X, & CD, G. (2007) *BIOPHYSICAL JOURNAL* 371A-371A
29. Xu, H. X., Wang, X. H., Persson, M. P., Xu, H. Q., Kall, M., & Johansson, P. (2004) Physical Review Letters 93.
30. Asian, K., Gryczynski, I., Malicka, J., Matveeva, E., Lakowicz, J. R., & Geddes, C. D. (2005) *Current Opinion in Biotechnology* 16, 55-62.
31. Asian, K., Wu, M., Lakowicz, J. R., & Geddes, C. D. (2007) *J Am Chem Soc* 129, 1524-1525.
32. Anantha, V. & Taflove, A. (2002) *Ieee Transactions on Antennas and Propagation* 50, 1337-1349.
33. Dolmans D E, Fukumura D, Jain R K (2003) Photodynamic therapy for cancer. Nat Rev Cancer 3(5):380-387.
34. Wilson B C (2002) Photodynamic therapy for cancer: principles. *Can J Gastroenterol* 16(6):393-396.
35. Vrouenraets M B, Visser G W M, Snow G B, Van Dongen G A M S (2003) Basic principles, applications in oncology and improved selectivity of photodynamic therapy. *Anticancer Res* 23:505-522.
36. Copending U.S. patent application Ser. No. 12/016,247 entitled "METAL-ENHANCED FLUORESCENCE NANOPARTICLES."
37. Copending U.S. patent application Ser. No. 11/917,804 entitled "METAL ENHANCED FLUORESCENCE-BASED SENSING METHODS."
38. Copending U.S. patent application Ser. No. 11/917,075 entitled "BIOASSAYS USING PLASMONIC SCATTERING FROM NOBLE METAL NANOSTRUCTURES."
39. Copending U.S. patent application Ser. No. 11/719,731 entitled "MICROWAVE ACCELERATED ASSAYS."
40. Copending U.S. patent application Ser. No. 11/718,560 entitled "METAL-ENHANCE FLUORESCENCE FROM PLASTIC SUBSTRATES."
41. Copending U.S. patent application Ser. No. 11/695,497 entitled "MICROWAVE ACCELERATED PLASMONICS."

That which is claimed is:

1. A method for photodynamic treatment to a site in a subject to cause a desired therapeutic change, comprising the steps of:
   (a) applying a photosensitizer complex to the treatment site in the presence of molecular oxygen, wherein the photosensitizer complex comprises:
      (i) a metallic core with an oxide containing surface coating, wherein the metallic core exhibits surface plasmons on excitation and wherein the surface coating has a thickness from 0.5 nm to 40 nm; and
      (ii) a photosensitizer compound, wherein the photosensitizer compound is attached to the surface coating that covers the metallic core or impregnated into the surface coating, wherein the photosensitizer compound is positioned on the surface coating or within the surface coating to position the photosensitizer compound at a distance from about 2 nm to about 10 nm from the metallic core to provide for coupling interaction between the photosensitizer compound and excited metallic surface plasmons; and
   (b) positioning a source of electromagnetic energy that generates electromagnetic energy having one or more emission wavelengths substantially equal to a wavelength of absorption of the photosensitive compound;
   (c) administering the electromagnetic energy to the site to increase triplet yield of the photosensitizer compound thereby coupling energy with the metallic surface plasmons and providing for increased singlet oxygen generation in the available molecular oxygen.

2. The method according to claim 1, wherein the oxide containing surface coating is a metal oxide or a metal oxide/polymer composite.

3. The method according to claim 1, wherein the metallic core has a diameter ranging from 50 to 130 nm in diameter.

4. The method according to claim 1, wherein the metallic core comprises silver, gold, platinum, aluminum, copper, zinc, palladium and composites thereof.

5. The method according to claim 1, wherein the surface coating further comprises at least one targeting moiety, attached to the surface coating, wherein the target moiety is specific for a specific tumor marker.

6. The method according to claim 1, wherein the metallic core is a geometric shape including spherical, elliptical, triangular, or rod shape.

7. A photosensitizer complex that enhances generation of singlet oxygen in molecular oxygen comprising:
   (a) a metallic core with an oxide containing surface coating, wherein the metallic core exhibits surface plasmons on excitation; and
   (b) a photosensitizer compound, wherein the photosensitizer compound is attached to the surface coating covering the metallic core or impregnated into the surface coating and wherein the photosensitizer compound is positioned on the surface coating or within the surface coating to position the photosensitizer compound at a distance from 2 nm to 10 nm from the metallic core to provide for coupling interaction between the photosensitizer compound and excited metallic surface plasmons, thereby generating singlet oxygen in adjacent molecular oxygen.

8. The photosensitizer complex according to claim 7, wherein the photosensitizer further comprises binding ligands attached to the surface coating or impregnated therein wherein the ligands have affinity for a receptor on a cell in need of photodynamic therapy.

9. The photosensitizer complex according to claim 7, wherein the surface coating is evenly distributed on the metallic core, in a pattern, or discontinuously distributed.

10. The photosensitizer complex according to claim 7, wherein the metallic core is a solid metallic sphere or a core of one material that is coated with a metallic surface.

11. The photosensitizer complex according to claim 7, wherein the metallic core has a diameter ranging from 2 nm to 150 nm.

12. The photosensitizer complex according to claim 7, wherein the metallic core is fabricated from any metal that provides for excitable plasmons.

13. The photosensitizer complex according to claim 12, wherein the metal is silver, gold, platinum, aluminum, copper, zinc, palladium or composites thereof.

14. The photosensitizer complex according to claim 7, wherein the photosensitizer is evenly distributed, randomly or patterned within or on the coating encompassing the metallic core.

15. The photosensitizer complex according to claim 7, wherein the surface coating further comprises at least one targeting moiety that is specific for a cancer-specific and/or pathogen-specific marker on a tumor.

16. A method of treating a host harboring tumor cells, the method comprising administering to the host at least a first agent in the presence of light and molecular oxygen, wherein the first agent comprises a photosensitizer complex comprising;

(a) a metallic core with an oxide containing surface coating, wherein the metallic core exhibits surface plasmons on excitation; and (b) a photosensitizer compound, wherein the photosensitizer compound is attached to the surface coating covering the metallic core or impregnated into the surface coating and wherein the photosensitizer compound is positioned on the surface coating or within the surface coating to position the photosensitizer compound at a distance from 2 nm to 10 nm from the metallic core to provide for coupling interaction between the photosensitizer compound and excited metallic surface plasmons, thereby generating singlet oxygen in adjacent molecular oxygen that is cytotoxic to the neoplastic tissue.

* * * * *